US010278649B2

(12) United States Patent
Hayat et al.

(10) Patent No.: US 10,278,649 B2
(45) Date of Patent: May 7, 2019

(54) METHODS AND SYSTEMS FOR DETECTING CANCER

(71) Applicant: STC.UNM, Albuquerque, NM (US)

(72) Inventors: Majeed M. Hayat, Albuquerque, NM (US); Sanjay Krishna, Albuquerque, NM (US); Sebastian Eugenio Godoy, Albuquerque, NM (US); David A. Ramirez, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 44 days.

(21) Appl. No.: 15/531,135

(22) PCT Filed: Nov. 24, 2015

(86) PCT No.: PCT/US2015/062500
§ 371 (c)(1),
(2) Date: May 26, 2017

(87) PCT Pub. No.: WO2016/086034
PCT Pub. Date: Jun. 2, 2016

(65) Prior Publication Data
US 2018/0333105 A1 Nov. 22, 2018

Related U.S. Application Data

(60) Provisional application No. 62/084,975, filed on Nov. 26, 2014.

(51) Int. Cl.
G06K 9/00 (2006.01)
A61B 5/00 (2006.01)
(Continued)

(52) U.S. Cl.
CPC ............ *A61B 5/7275* (2013.01); *A61B 5/015* (2013.01); *A61B 5/444* (2013.01); *A61B 5/7264* (2013.01);
(Continued)

(58) Field of Classification Search
None
See application file for complete search history.

(56) References Cited

U.S. PATENT DOCUMENTS

2004/0236225 A1 11/2004 Murphy et al.
2007/0073156 A1 3/2007 Zilberman et al.
(Continued)

FOREIGN PATENT DOCUMENTS

JP 2002-512070 A 4/2002
WO WO 99/53840 10/1999
WO WO 2016/086034 * 6/2016

OTHER PUBLICATIONS

Kim (PCT Officer), PCT International Search Report and the Written Opinion of the International Searching Authority dated Mar. 15, 2016, International Application No. PCT/US2015/062500, pp. 1-10.

*Primary Examiner* — Delomia L Gilliard
(74) *Attorney, Agent, or Firm* — MH2 Technology Law Group, LLP

(57) ABSTRACT

A technique for classifying lesions as malignant or benign is disclosed. The technique can include: cooling an area of skin including a lesion of a patient to initiate a warm-up process; receiving a temporal sequence of thermal images of the area of skin representing a thermal recovery of the area of skin, the temporal sequence of thermal images generated by an infrared camera; generating a temporal profile of the thermal recovery based on the temporal sequence of thermal images; analyzing temporal statistical properties of the temporal profile; determining a malignancy probability that the lesion is malignant based on an analysis of the temporal profile, wherein the determining includes extracting one or more statistical features based on continuous-time stochastic signals in the sequence of thermal images; and classifying the lesion based on the malignancy probability.

20 Claims, 14 Drawing Sheets

(51) Int. Cl.
- *A61B 5/01* (2006.01)
- *G06F 19/00* (2018.01)
- *G06T 7/62* (2017.01)
- *G06T 7/68* (2017.01)
- *G06T 7/277* (2017.01)
- *G06T 7/13* (2017.01)
- *G06T 7/174* (2017.01)
- *G06T 7/90* (2017.01)
- *G16H 50/20* (2018.01)
- *G06K 9/62* (2006.01)
- *G06T 7/00* (2017.01)
- *G06T 7/40* (2017.01)

(52) U.S. Cl.
CPC ........... *G06F 19/00* (2013.01); *G06K 9/6214* (2013.01); *G06K 9/6277* (2013.01); *G06T 7/0016* (2013.01); *G06T 7/13* (2017.01); *G06T 7/174* (2017.01); *G06T 7/277* (2017.01); *G06T 7/40* (2013.01); *G06T 7/62* (2017.01); *G06T 7/68* (2017.01); *G06T 7/90* (2017.01); *G16H 50/20* (2018.01); *A61B 5/489* (2013.01); *G06T 2207/10016* (2013.01); *G06T 2207/10048* (2013.01); *G06T 2207/30088* (2013.01); *G06T 2207/30096* (2013.01)

(56) References Cited

U.S. PATENT DOCUMENTS

| | | | |
|---|---|---|---|
| 2009/0216130 A1 | 8/2009 | Hirsch et al. | |
| 2009/0318815 A1* | 12/2009 | Barnes | A61B 5/742 600/473 |
| 2009/0326383 A1* | 12/2009 | Barnes | A61B 5/0059 600/476 |
| 2013/0116573 A1 | 5/2013 | Herman | |
| 2014/0378810 A1* | 12/2014 | Davis | G06T 16/245 600/407 |

\* cited by examiner

METHODS AND SYSTEMS FOR DETECTING CANCER

CROSS-REFERENCE TO RELATED APPLICATIONS

This application claims priority to, and the benefit of PCT Patent Application No. PCT/US2015/062500 filed on Nov. 24, 2015, which claims priority to, and the benefit of U.S. Provisional Application No. 62/084,975, entitled "METHODS AND SYSTEMS FOR DETECTING CANCER" and filed Nov. 26, 2014, the entirety of which is hereby incorporated by reference.

GOVERNMENT SUPPORT STATEMENT

This invention was made with Government support under Grant No. DE-NA0002494 awarded by the U.S. Department of Energy. The U.S. Government has certain rights in this invention.

TECHNICAL FIELD

The present disclosure relates generally to the field of cancer detection, and more particularly, to methods and systems for detecting skin cancer by applying statistical decision theory and image-processing techniques to dynamic infrared image sequences.

BACKGROUND

The prevalence of skin cancer is increasing worldwide, with epidemic levels present in North America, Europe and Australia. For example, skin cancer is the most common cancer in the United States with over 3.5M million annual cases. Statistics from the American Cancer Society indicate that 20% of the American population will develop this disease during their lifetime.

Skin cancer is unusually complex and difficult to diagnose, and current clinical practice relies on highly subjective visual methods for detection. Presently, visual inspection by a dermatologist has good sensitivity (>90%) but poor specificity (<10%), especially for melanoma, which leads to a high number of unnecessary biopsies. Further, it is estimated that dermatologists miss about one third of curable melanomas, which is the most deadly form of skin cancer. Missing a curable melanoma delays treatment and can lead to metastatic cancer, which has a five-year survival rate of less than 15%, and it can cost upwards of $170,000 per case to treat compared to $1,800 in the case of lesion-removal surgery if caught early. Physicians have employed noninvasive skin-cancer screening and diagnostic aids with limited success because most of them do not provide substantial improvements in diagnostic accuracy beyond the existing visual methods.

It is estimated that about 10.6 million excess skin cancer biopsies are done in the United States (US) per year. If the laboratory and medical doctor (MD) payment rate for Medicare (Code 88305=$70 for laboratory and Code 11100=$90 for MD) is considered, the 100% addressable U.S. market for excess skin biopsies is around $1.7B/year. Further, the yield of skin cancer biopsies performed to diagnose cancer is quite low, with 30 benign lesions biopsied for every one melanoma, and three benign lesions biopsied for each non-melanoma skin cancer such as basal cell carcinoma (BCC) and squamous cell carcinoma (SCC). In addition to the cost burden to payers, the excess biopsies are a source of patient discomfort, which may discourage patients from seeking help from a specialist.

The medical community has been pursuing non-invasive and early detection of skin cancer based on thermal imaging. One of the approaches is to make a decision whether the lesion is benign or malignant based on a sequence of thermal-images obtained of the lesion after it is cooled substantially, then removing the cooling source and allowing the tissue to naturally warm up back to the body temperature.

Improved skin cancer detection methods, and systems for performing the improved methods, would be desirable.

SUMMARY

The following presents a simplified summary in order to provide a basic understanding of some aspects of one or more embodiments of the present disclosure. This summary is not an extensive overview, nor is it intended to identify key or critical elements of the present disclosure, nor to delineate the scope of the disclosure. Rather, its primary purpose is merely to present one or more concepts in simplified form as a prelude to the detailed description presented later.

Disclosed skin cancer detection methods and systems utilize a physical model for the warming-up process, also referred to as the thermal-recovery process, represented by the thermal image sequence described above, in conjunction with an automated, mathematical decision-making algorithm, to identify lesions as malignant or benign. The disclosed methods and systems can be used to perform preliminary cancer detections, specifically, to aid health care professionals in deciding whether or not a patient needs to perform biopsy. The successful application of the disclosed methods and systems can reduce the number of biopsies.

According to some embodiments, a method for classifying lesions is disclosed. The method includes cooling an area of skin including a lesion of a patient to initiate a warm-up process; receiving a temporal sequence of thermal images of the area of skin representing a thermal recovery of the area of skin, the temporal sequence of thermal images generated by an infrared camera; generating a temporal profile of the thermal recovery based on the temporal sequence of thermal images; analyzing temporal statistical properties of the temporal profile; determining a malignancy probability that the lesion is malignant based on an analysis of the temporal profile, wherein the determining includes extracting one or more statistical features based on continuous-time stochastic signals in the sequence of thermal images; and classifying the lesion based on the malignancy probability.

Various optional features of the above embodiments include the following. The continuous-time stochastic signals may include at least one multidimensional continuous-time signal, and the extracting one or more statistical features may further include extracting a boundary of the lesion based on the at least one multidimensional continuous-time signal. The one or more statistical features may include spatial information of the lesion, and the spatial information of the lesion may include at least one of a symmetry of the lesion, a border of the lesion, one or more colors within the lesion, a number of different colors within the lesion, a diameter of the lesion, or a texture of the lesion. The method may include generating a stochastic parametric description of the warm-up process. The method may include estimating an autocorrelation function for the warm-up process; estimating eigenfunctions and eigenvalues of the autocorrelation function of the warm-up process; extracting Karhunen-Loève coefficients for the warming-up process based on the eigenfunctions; and extracting projections of the warming-up profile onto temporal or spatio-temporal basis functions including the eigenfunctions. The method may include modeling parameters of the autocorrelation function for the warm-up process using a multivariate random distribution model. The determining a malignancy probability may further include: providing a predetermined number of eigenvalues and eigenfunctions from the autocorrelation function; and forming a likelihood-ratio test. The predetermined number of eigenvalues and eigenfunctions may be a whole number greater than one. The temporal profile may include a plurality of temperature gradients of the lesion. The classifying the lesion may further include classifying the lesion as at least one of a benign type or a malignant type.

According to various embodiments, a system for classifying lesions is presented. The system includes a cooling unit configured for applying to an area of skin including a lesion of a patient to initiate a warm-up process; an infrared camera configured to receive a temporal sequence of thermal images of the area of skin representing a thermal recovery of the area of skin; and an electronic computer communicatively coupled to the infrared camera and configured to generate a temporal profile of the thermal recovery based on the temporal sequence of thermal images, analyze temporal statistical properties of the temporal profile, determine a malignancy probability that the lesion is malignant based on an analysis of the temporal profile by extracting one or more statistical features based on continuous-time stochastic signals in the sequence of thermal images, and classify the lesion based on the malignancy probability.

Various optional features of the above embodiments include the following. The continuous-time stochastic signals may include at least one multidimensional continuous-time signal, and the computer may be further configured to extract the one or more statistical features by extracting a boundary of the lesion based on the at least one multidimensional continuous-time signal. The one or more statistical features may include spatial information of the lesion, and the spatial information of the lesion may include at least one of a symmetry of the lesion, a border of the lesion, one or more colors within the lesion, a number of different colors within the lesion, a diameter of the lesion, or a texture of the lesion. The computer may be further configured to generate a stochastic parametric description of the warm-up process. The computer may be further configured to: estimate an autocorrelation function for the warm-up process; estimate eigenfunctions and eigenvalues of the autocorrelation function of the warm-up process; extract Karhunen-Loève coefficients for the warming-up process based on the eigenfunctions; and extract projections of the warming-up profile onto temporal or spatio-temporal basis functions including the eigenfunctions. The computer may be further configured to model parameters of the autocorrelation function for the warm-up process using a multivariate random distribution model. The system may be further configured to determine a malignancy probability by: providing a predetermined number of eigenvalues and eigenfunctions from the autocorrelation function; and forming a likelihood-ratio test. The predetermined number of eigenvalues and eigenfunctions may be a whole number greater than one. The temporal profile may include a plurality of temperature gradients of the lesion. The computer may be further configured to classify the lesion by classifying the lesion as at least one of a benign type or a malignant type.

BRIEF DESCRIPTION OF THE DRAWINGS

The accompanying drawings, which are incorporated in and constitute a part of this specification, illustrate embodiments of the present disclosure and together with the description, serve to explain the principles of the disclosure. In the figures.

Figure 1:
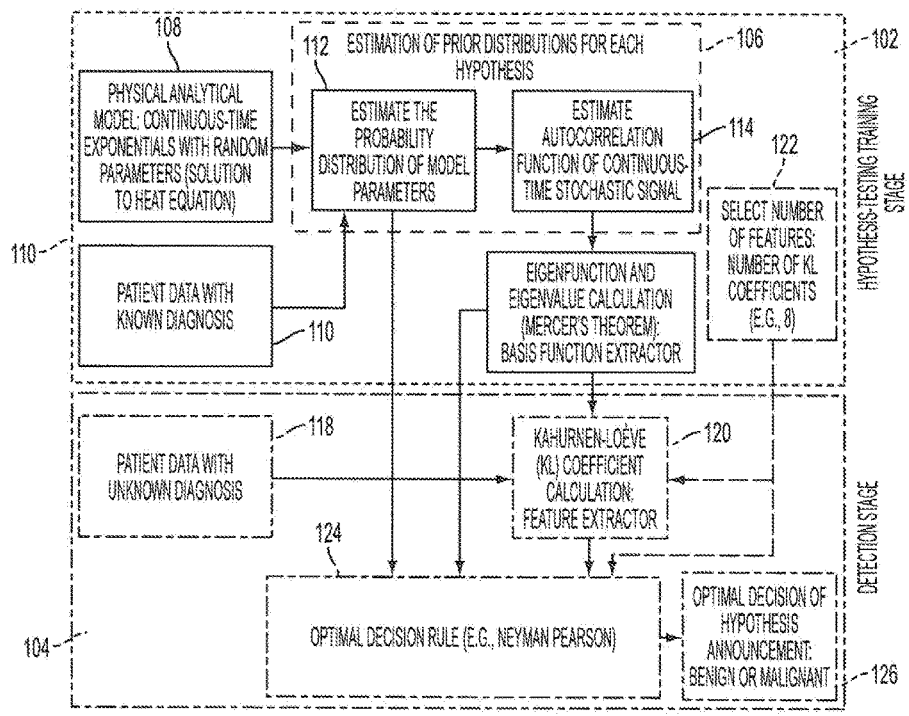
FIG. 1 is a block diagram of an example process performed by an example cancer detection system and method that analyzes dynamic infrared image sequences to detect skin cancer and other malignant growths, consistent with various embodiments.

It should be noted that some details of the Figures have been simplified and are drawn to facilitate understanding of the present disclosure rather than to maintain strict structural accuracy, detail, and scale.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or like parts.

I. Introduction

Some embodiments utilize dynamic thermal imaging (DTI) to demonstrate a rapid, accurate and non-invasive imaging system for detection of skin cancer. The lesion is cooled down and the thermal recovery is recorded using infrared imaging. The thermal recovery curves (TRCs) of the suspected lesions are then analyzed using an algorithm derived based on statistical-detection theory for continuous-time stochastic processes in conjunction with a physics-based probabilistic model for the TRCs.

In more detail, some embodiments employ an algorithm that uses DTI combined with a communication-theoretic approach known as statistical detection theory. DTI is a technique in which a thermal stimulus is applied to a suspicious lesion and the thermal recovery is captured as a function of time by means of infrared imaging. This procedure generates a sequence of infrared images that are registered and calibrated for radiometric accuracy.

Even though the thermal recovery for a skin-cancer lesion may be different from that for the surrounding healthy skin, prior art methods generally extract only a fraction of the information present in the temporal evolution of the thermal recovery process because they neglect the inherent temporal statistical features. To overcome this, some embodiments extract the statistical information present in the thermal recovery process—information that is vital for making a decision regarding malignancy of the lesion—by characterizing the process as a random function of time, or a continuous-time stochastic process. This complete statistical understanding of the thermal recovery process is utilized in a statistical-inference approach that yields an optimal decision rule for classifying a lesion as malignant or benign.

The inventors undertook a real-world implementation of an embodiment. The TRC model was obtained from a heat equation and used to derive parametric analytical autocorrelation functions whose parameters are estimated from patients with known conditions. An optimal statistical decision rule was then derived for which the sensitivity is guaranteed to be at a maximum for every prescribed false-alarm probability. The algorithm was trained using TRCs from 110 human subjects and tested on 30 human subjects with unknown diagnosis. All the malignant subjects were correctly identified (100% sensitivity) for a false-alarm probability below 1% (specificity>99%). Robustness analysis was undertaken with various permutations of test and training datasets, and under different selections of the lesion boundaries. The maximum variability in the sensitivity of the method was 3% and 0.1%, respectively, for 200 different random permutations in selecting the training set and different radii of the region that determine the lesion boundary. To the best of the inventors' knowledge, this is the highest reported accuracy and robustness for any non-invasive method for detection of skin cancer.

FIG. 1 is a block diagram of an example process performed by an example cancer detection system that analyzes dynamic infrared image sequences to detect skin cancer and other malignant growths, consistent with various embodiments. In particular, FIG. 1 depicts three main stages. Signal modeling stage 106, described in detail in Section II, includes the portion of the process that involves determining signal properties for both malignant and benign lesions. Hypotheses testing and training stage 102, described in detail in Section III, includes the portion of the process that involves building a model that utilizes data produced by signal modeling stage 106. Detection stage 104, described in detail in Section IV, includes the portion of the process that categorizes patient data with an unknown diagnosis (block 118) as either likely malignant or benign.

II. Signal Modeling Stage

This section explains how the signal is modeled by the physics of the problem according to some embodiments. That is, this section describes signal modeling stage 106 of FIG. 1. The general assumptions made in the problem and other parameters are also stated.

Figure 5:
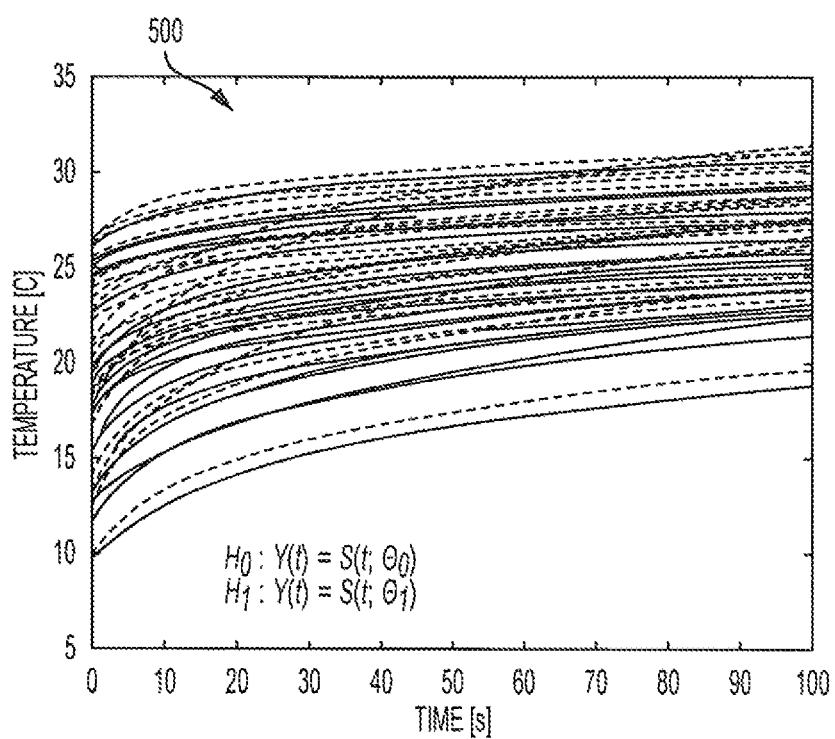
FIG. 5 depicts a set of thermal recovery curves for a set of patients obtained using an infrared camera, consistent with various embodiments.
Figure 6:
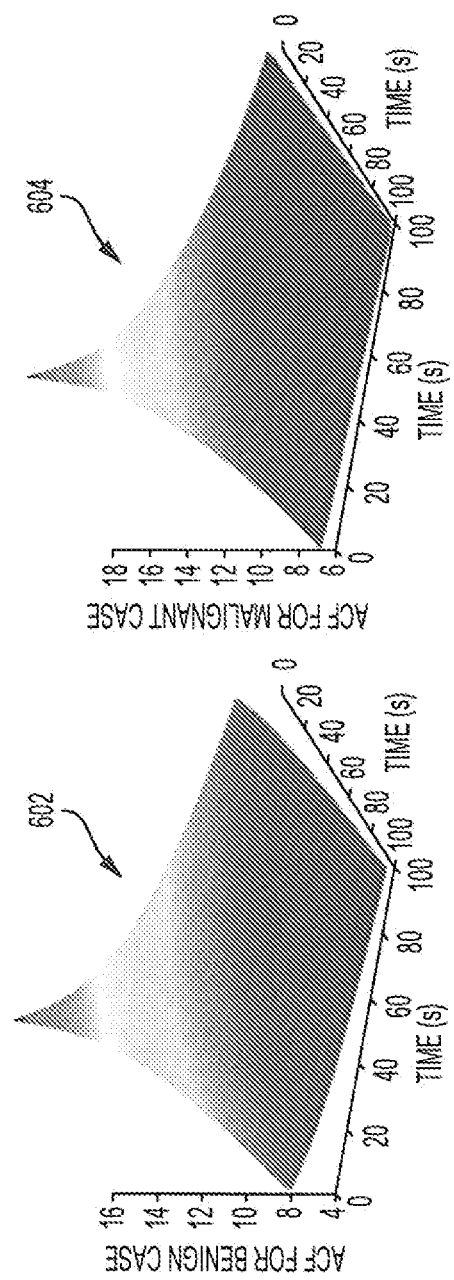
FIG. 6 depicts graphs representing example autocorrelation functions computed under hypotheses for benign and malignant tumors, consistent with various embodiments.

The malignancy of a suspicious lesion can be inferred from the temporal information contained in the thermal recovery curves (TRCs) averaged over all the pixels within the lesion boundary. Such an aggregate TRC, generally referred to as a "TRC", tends to offset the effects of anomalous TRCs (e.g., TRCs corresponding to healthy tissue that may be sparsely dispersed amidst malignant tissue). FIG. 5 depicts representative TRCs 500 for seventy patients under two hypotheses: $H_0$, representing patients with benign conditions, and $H_1$ representing patients with malignant conditions. The TRCs under each hypothesis are modeled using a stochastic process with a mathematical structure that is inherited from an analytical solution of a heat equation (block 108 of FIG. 1). Each stochastic process is parameterized by five random variables that account for the model unknowns and uncertainties. The statistical correlations amongst these components are exploited by computing the autocorrelation function (ACF) of the TRCs under each hypothesis, as depicted in FIG. 6.

Thus, some embodiments utilize the heat equation, representing the evolution of the temperature of the tissue of interest, to model the physical thermal response of the skin. The heat equation may be used in various embodiments and the approach can be used for a different model without a loss of generality. Note that in general, the multilayer bioheat equation is ill-posed to solve if only knowledge of surface temperature (measured by the thermal image-sequence) is assumed. Nevertheless, the skin has an emissivity≥0.98, so all the subcutaneous thermal processes may be integrated to the surface by thermal diffusion (i.e., the skin can be assumed to mimic a blackbody source). Therefore, the heat equation model can be postulated as a valid model considering the physics of the problem, where an effective diffusivity constant will account for all of the subcutaneous thermal processes that are integrated to the surface. In the prior art, the probability distribution of the effective diffusivity has been an unknown, random parameter. With the present approach, its probability density function and expected value can be estimated from the signal modeling.

Some embodiments solve the heat equation as presently applied analytically. Using the boundary conditions, it was found that the thermal recovery is modeled by a function of time that contains multiple exponential functions. Under different initial conditions (an unknown function) it was found that two exponential functions plus a constant were sufficient to model the thermal recovery; nevertheless, the expert can easily extend this model to include more exponential functions if the taught approach does not match a prescribed accuracy.

III. Hypothesis-Testing Training Stage

This section describes a hypothesis testing stage according to some embodiments. That is, this section describes signal modeling stage 102 of FIG. 1. Some embodiments address the detection of malignant lesion by testing different hypotheses. The following is explained for the case of testing two hypotheses, namely the average thermal recovery of the lesion is benign, versus the average thermal recovery of the lesion is malignant. The protocol can be extended to multiple hypotheses comprising, for example, different sub-classes of benign and/or malignant cases.

To summarize: Starting from the stochastic model for the TRCs, utilize the TRCs of patients with known conditions to determine the distributions of each parameter and the correlations therein within the model. Each pixel within the suspected lesion will generate a realization of the random processes under the corresponding hypothesis. These realizations are used to compute the mean of each parameter as well as the pairwise cross-covariance between the parameters that determine the ACF under each hypothesis. The integral equation that defines the eigenvalues and eigenfunctions (e.g., a Fredholm equation of the second kind) are solved numerically by the Nystrom method, in which, by a quadrature rule, one approximates the integral equation by an equivalent matrix eigenvalue problem. The eigenvectors are the sampled versions of the corresponding eigenfunctions, which are sampled at the grid points defined by the quadrature rule. The eigenvalues are sorted in decreasing order and stored with their corresponding eigenfunctions. The sorted eigenvalues with its corresponding eigenfunctions may be referred to as the eigenvalue-eigenfunction pairs, or eigenpairs for short. For a prescribed fixed false-alarm probability, the optimum threshold is defined for different levels of granularity, as defined by the number of eigenvalue-eigenfunction pairs stored. With this, the classification of a patient with an unknown condition may proceed.

A more detailed description of the hypothesis-testing training stage follows.

The following points include some considerations and the assumptions made for addressing the detection problem according to some embodiments. Statistical detection theory for continuous-time stochastic signals is employed, i.e., each hypothesis (benign or malignant) has its own stochastic signal as a function of time over the span of the thermal-image sequence. The continuous-time signal model under each hypothesis has a deterministic temporal functional form, but the functional form may be parameterized by random parameters in the form of correlated random variables.

The deterministic form is the signal model presented herein, e.g., in Section II, above, i.e., two exponential functions plus a constant. Each model may have five random parameters: the unknown constant, the unknown coefficients of each exponential function, and the unknown time constants of the exponentials. Some embodiments assume that under each hypothesis, these five random parameters of the stochastic continuous-time model are samples of a joint probability distribution that is specific to each of the two hypotheses.

Thermal-image data from each patient produces a continuous-time signal model and its random parameters are assumed to be realizations of the joint probability distribution of these parameters under the appropriate hypothesis. The probability distribution of the parameters may be estimated (block 112 of FIG. 1) from the realizations collected from multiple patients with known condition of their lesion being benign or malignant. From the inventors' experience, 110 patients (a combination of benign and malignant cases) are sufficient (block 110 of FIG. 1).

The autocorrelation function, under each hypothesis, whose form is analytically determined by the inventors in terms of the joint pairwise moments of the five random variables, is further calculated from the corresponding estimated distributions of the patient parameters. (See block 114 of FIG. 1) The autocorrelation function describes the correlation between the values of the characteristic signal of each hypothesis at two different instants of time. It characterizes, to a good extent, the inherent random processes under each hypothesis and it sets up the application of Mercer's theorem (block 116 of FIG. 1) and the Karhunen-Loève expansion (block 120 of FIG. 1).

With the estimated autocorrelation function at hand, the Karhunen-Loève expansion is employed to convert the statistical hypothesis-testing problem from that of a continuous-time signal to that of an infinite sequence of random variables. The signal parameterization in conjunction with the Karhunen-Loève expansion (block 120 of FIG. 1) and Mercer's theorem (block 116 of FIG. 1) together permit presenting the detection problem based on the eigenfunctions and eigenvalues of each autocorrelation function under the appropriate hypothesis. Specifically, for a data set comprising thermal images for any patient with known diagnosis, with the data possibly, but not necessarily, averaged over all pixels, is correlated with each eigenfunction resulting in a sequence (infinite in principle) of features that are collectively and statistically equivalent to the entirety of the thermal-image-sequence data.

In more detail, some embodiments solve the hypothesis-testing problem associated with the TRCs following a continuous-time Karhunen-Loève (KL) approach, which is optimal in the sense of extracting all the statistical features present in the TRCs. Specifically, convert each continuous-time TRC to a statistically equivalent sequence of uncorrelated random variables, known as the KL coefficients. The KL coefficients are then computed from each TRC in conjunction with the eigenvalue-eigenfunction pairs associated with each ACF.

Figure 7:
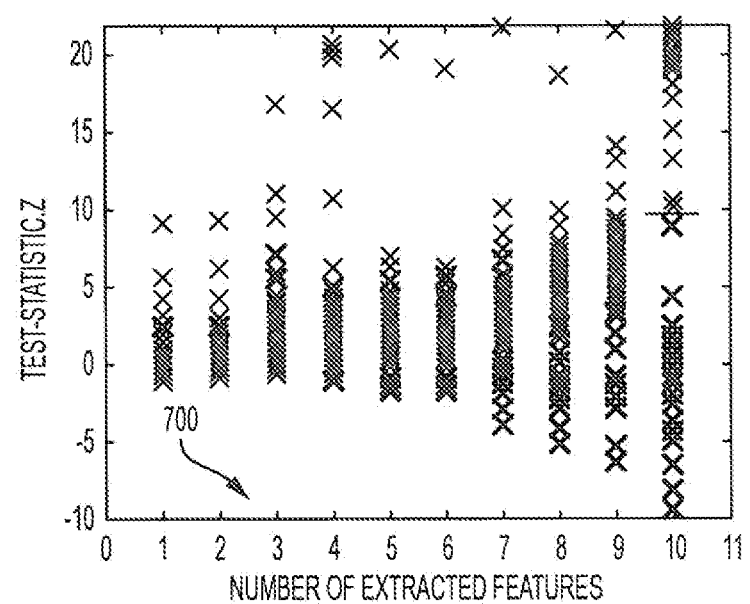
FIG. 7 depicts a graph representing example test statistics for various numbers of extracted features, consistent with various embodiments.

Next, employ optimal-inference theory to announce the hypothesis based on the KL coefficients of an observed TRC. This may be accomplished by comparing the so-called test-statistic, which is calculated from the likelihood ratio associated with the sequence of KL coefficients, to an optimally selected threshold. Thus, some embodiments map each TRC to a single number, namely the test-statistic, which compactly contains all the temporal statistical information that determines the malignancy of the suspicious TRC. Each column of the chart 700 of FIG. 7, for example, shows the values of the test-statistics corresponding to the TRCs 500 in FIG. 5 for different numbers of the KL coefficients (see block 122 of FIG. 1) in computing the test-statistic. The value of each test-statistic is then compared to an optimally selected threshold, and the result of the comparison dictates which hypothesis each TRC belongs to.

In selecting the decision threshold, some embodiments use the Neyman-Pearson (NP) decision rule (block 124 of FIG. 1), in which the threshold is selected so as the theoretically calculated detection probability is maximized while keeping the false-alarm probability below a prescribed level of our choice. Thus, a Neyman-Pearson decision rule, which maximizes the probability of detecting malignant lesions while keeping the false-alarm rate (probability) at a prescribed, fixed level, is derived. This decision rule employs the sequence of features extracted from projecting the thermal recovery curve onto the eigenfunctions using integration (e.g., 10 eigenfunctions), it computes the test-statistic using the projections in conjunction with the eigenvalues, it computes the probability distribution of the test-statistic under each hypothesis, and it provides the decided-upon hypothesis by comparing the test-statistics with a decided-upon threshold based on a prescribed optimality criterion. The decision rule may be implemented and tested using the hypothesis-testing procedure described herein.

This completes the training stage of the algorithm and development of the lesion classifier, which includes the determination of the eigenvalue-eigenfunction pairs associated with the ACF under each hypothesis, the number of required KL coefficients, the formula for the test-statistic, and the optimal decision threshold.

IV. Detection Stage

Figure 8:
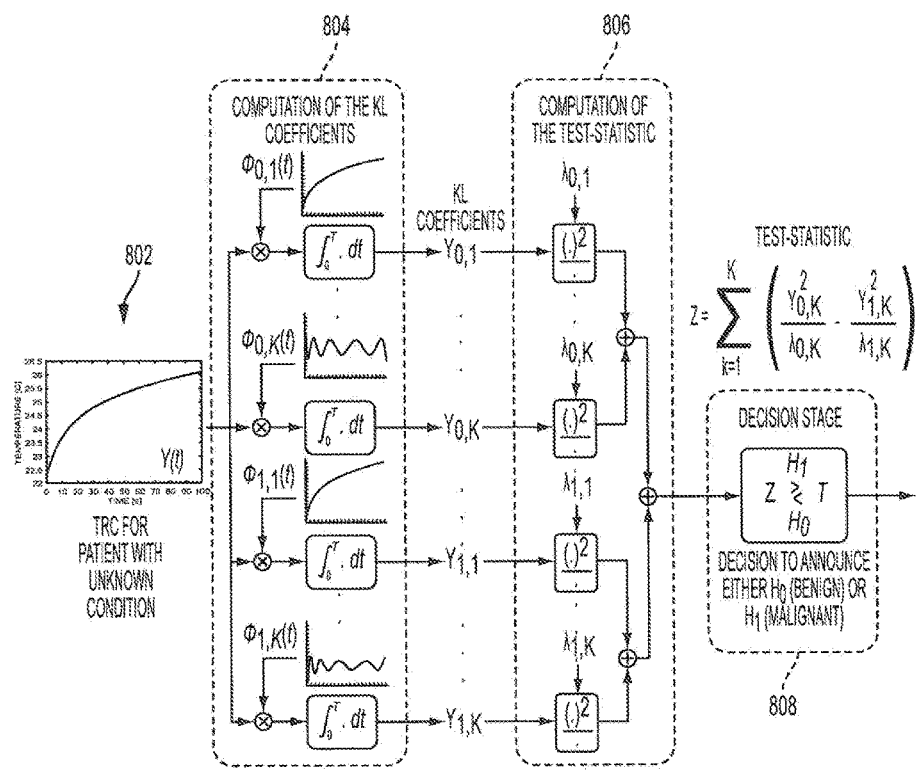
FIG. 8 is a schematic diagram depicting a decision-making stage, consistent with various embodiments.

This section describes how the algorithm is utilized to infer whether a patient's lesion is malignant or benign (block 104 of FIG. 1). For a patient with unknown diagnosis (block 118 of FIG. 1, block 802 of FIG. 8) and measured TRC Y(t), some embodiments first compute the KL coefficients (statistical features) (block 804 of FIG. 8) associated with Y(t) by computing its inner product (i.e., projections) with each of the eigenfunctions from the training stage, which describe each hypothesis. That is, using stored eigenfunctions, compute the KL coefficients of the TRC by using both sets of eigenfunctions $Y_{j,k} = \int Y(t)\phi_{j,k}(t)dt$, for j=0, 1 and k=1, 2, ... K. Second, some embodiments insert these coefficients in the formula of the test-statistic to obtain a random variable of the patient. That is, the statistical features are combined together with the corresponding eigenvalues to form the test-statistic for each TRC. Third, compare the test-statistic with the optimal decision threshold and declare (block 126 of FIG. 1, block 808 of FIG. 8) the lesion as malignant if the test-statistic exceeds the threshold. In other words, the test-statistic is then compared to the Neyman-Pearson decision threshold to declare the diagnosis of the patient as benign or malignant.

In more detail, once the autocorrelation functions are estimated and the Karhunen-Loève expansion is applied to the problem, the protocol for analyzing the data may be as follows, according to some embodiments. For a patient with unknown diagnosis (block 118 of FIG. 1, block 802 of FIG. 8), obtain the parameters of the signal model as explained in Section II above. Utilize the eigenfunctions and eigenvalues of each hypothesis (as explained in Section III) to compute the test statistics of the patient. Compute the threshold depending on the optimality criteria used and use it to compare the test statistic to. If using a Neyman-Pearson decision rule, apply threshold that is defined by the specified false-alarm probability.

Figure 2:
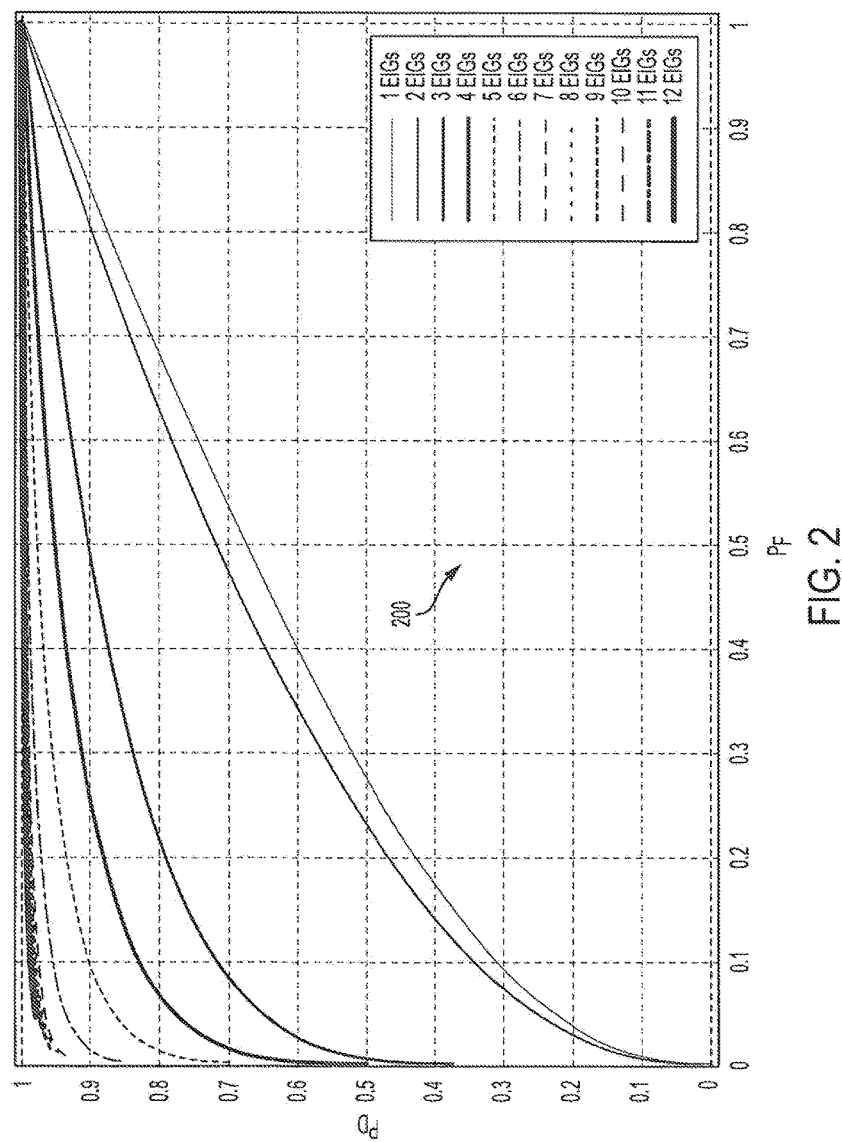
FIG. 2 shows representative theoretical receiver operating characteristic curves for the cancer detection system when using various numbers of eigenfunctions in detecting skin cancer and other malignant growths, consistent with various embodiments.

For a dataset of actual patient data comprising 140 subjects (with benign and malignant cases), the inventors used 110 of the patient data to train the hypothesis-testing stage. In FIG. 2, the theoretical receiver-operating characteristic (ROC) curve 200 is depicted for the case of a Neyman-Pearson decision rule. The number of eigenfunctions and eigenvalues used in the problem is incrementally changed from five to 10 functions to generate FIGS. 3A-F (302, 304, 306, 308, 310, 312).

Figure 3A:
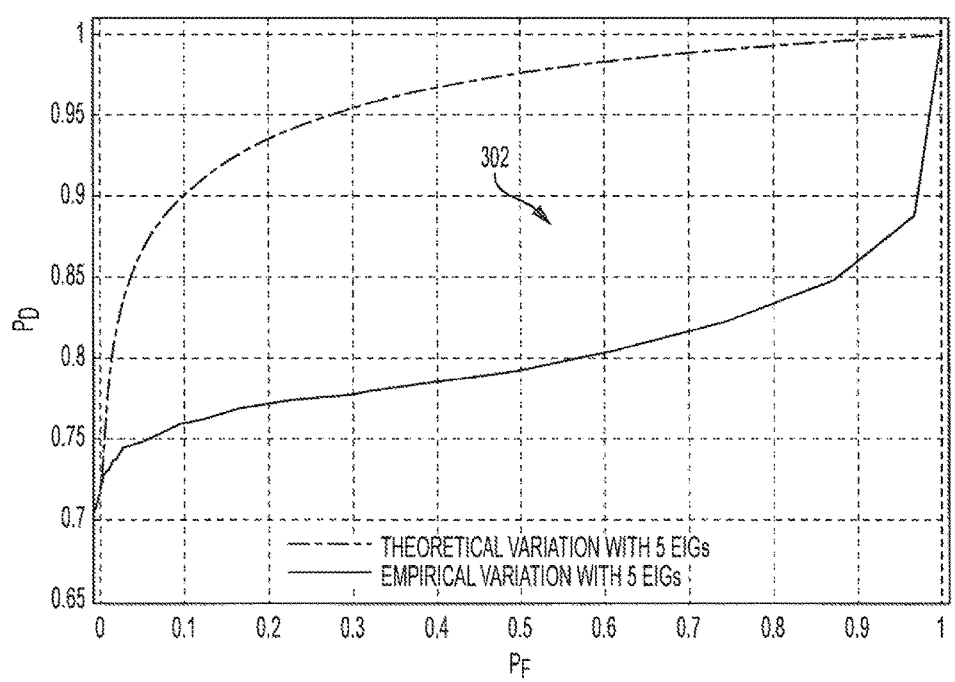
FIGS. 3A, 3B, 3C, 3D, 3E, and 3F show representative theoretical and experimental receiver operating characteristic curves for the cancer detection system when using various numbers of eigenfunctions in detecting skin cancer and other malignant growths, consistent with various embodiments.
Figure 3B:
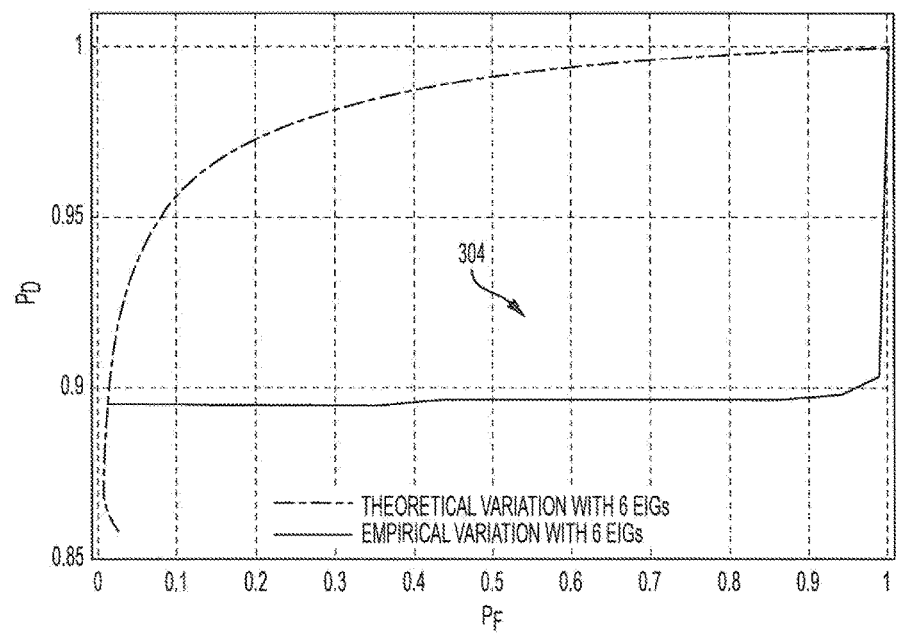
Figure 3C:
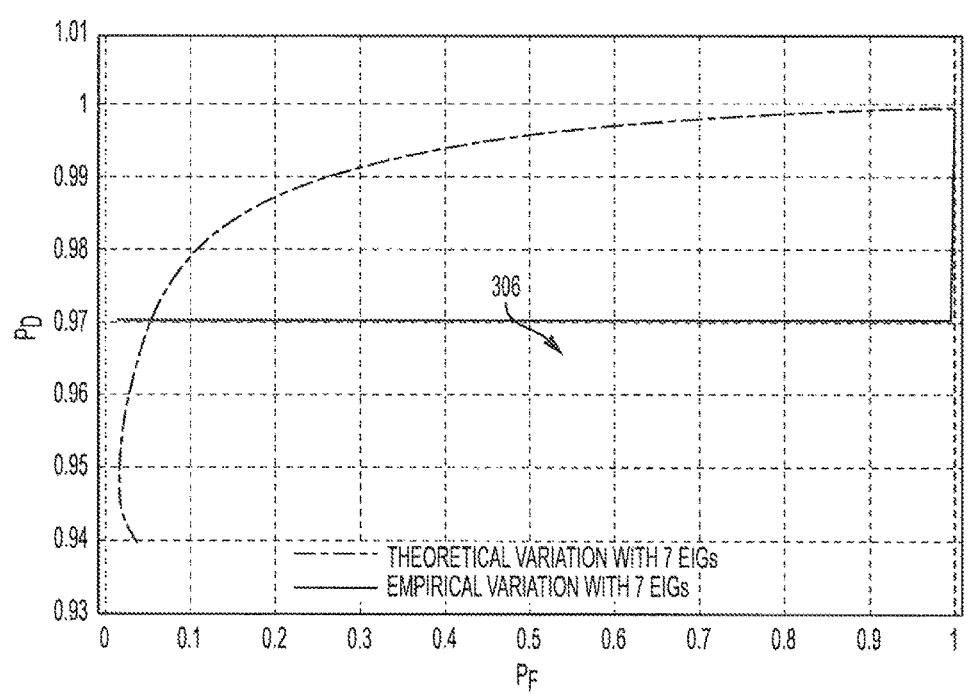
Figure 3D:
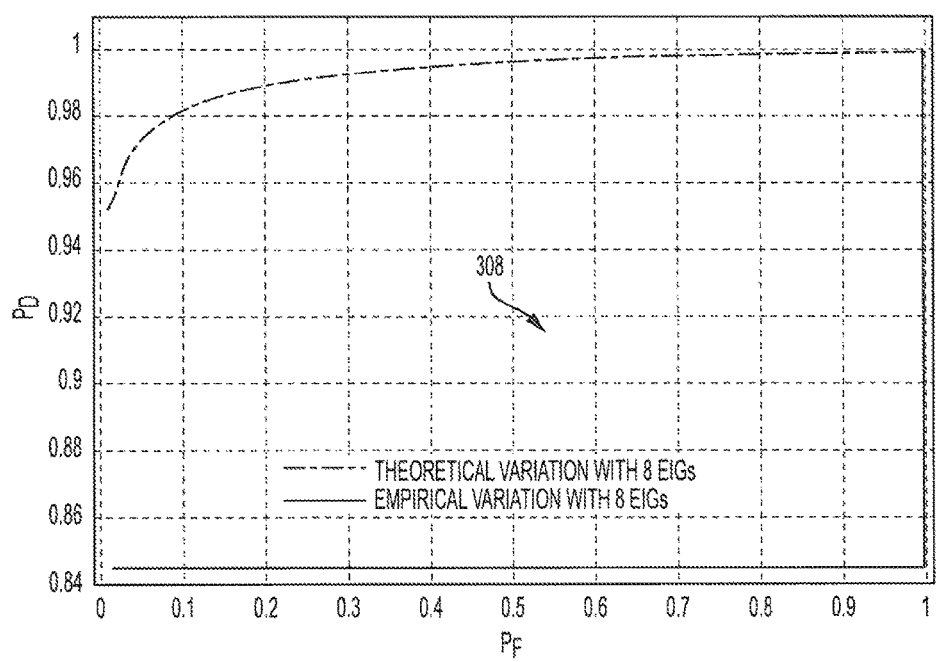
Figure 3E:
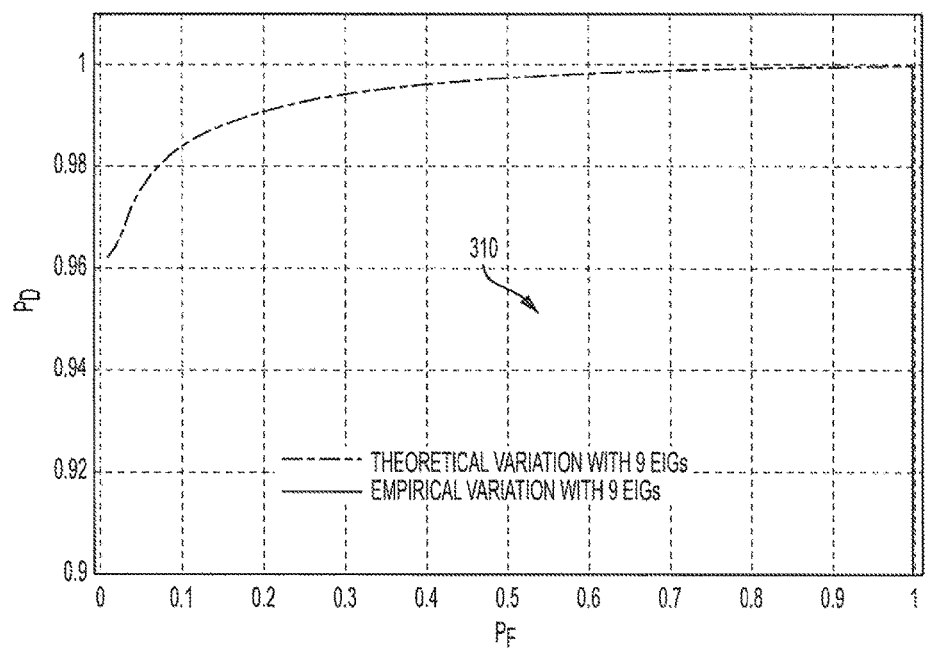
Figure 3F:
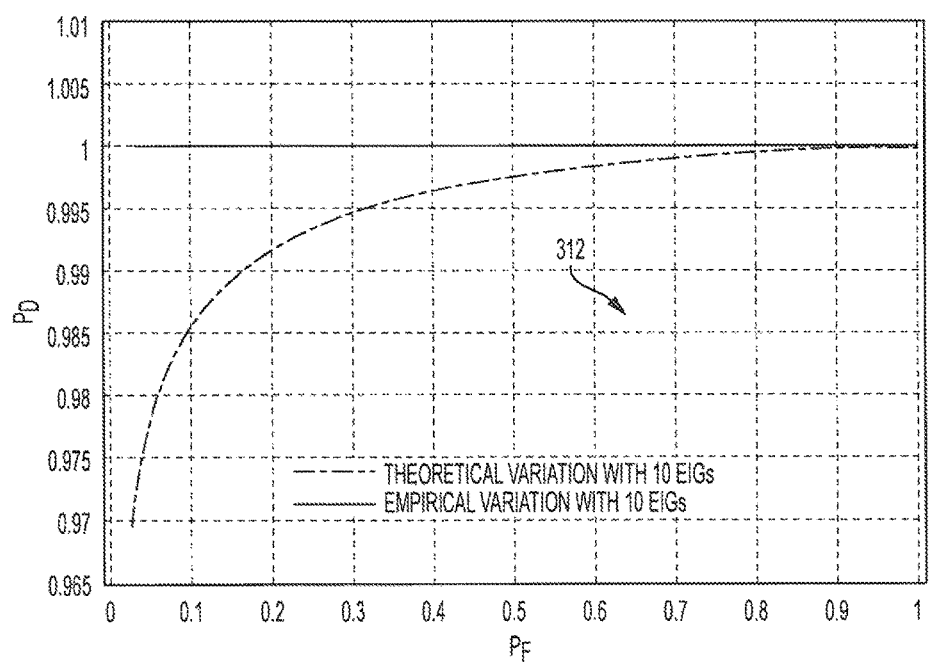
Figure 4:
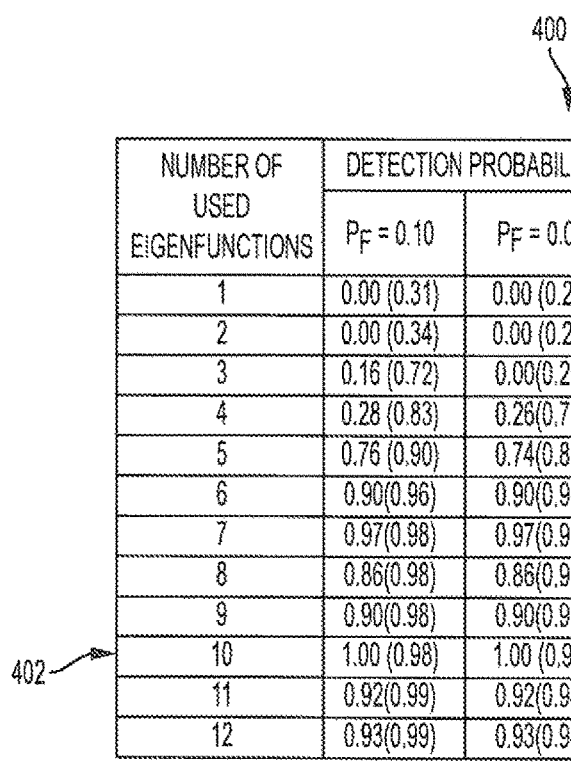
FIG. 4 shows a table summarizing representative performance of different levels of prescribed false-alarm probabilities, consistent with various embodiments.

Using the remaining 30 of the patient data, the inventors computed experimental ROC curves. For example, when ten eigenfunctions are used for a prescribed false-alarm probability of 0.01 (i.e., a prescribed specificity of 0.99) the detection probability is 0.9729, as shown in FIG. 3C. (See also chart 400 of FIG. 4, row 402). Due to the small number of patient data for testing, the experimental probability of detection for the same prescribed false-alarm probability is one (100%).

V. Experimental Results

The inventors conducted a cohort study of 140 adult human subjects to evaluate an embodiment. A description of methods and equipment follows.

Patient data acquisition equipment included three components. First, a cooling unit that is used to impart a thermal stimulus to the lesion and the surrounding skin tissue; the cooling unit was a Ranque-Hilsch vortex tube that generates an oil-free, moisture-free, ultra-quiet airflow. Second, an infrared marker, which is used for correction of involuntary movement of the subject (image registration); the marker was a square piece of plastic with a square opening in the middle. Third, the imaging portion of the system includes a commercial visible camera to capture a reference image before the thermal-image acquisition commences and a longwave infrared (LWIR) camera to capture the thermal recovery of the skin after the cool air supply is halted. The LWIR camera used a 320×256 focal-plane array (FPA) of quantum-well infrared photodetectors (QWIP) operating at 60K. The noise equivalent temperature difference (NEDT) of the FPA is 20 mK and the QWIP camera is fitted with a 50 mm, f/2 LWIR lens, yielding an approximate spatial resolution of 300 microns per pixel.

After informed consent, each subject was escorted to a designated room in the University of New Mexico Dermatology Clinic to perform the imaging procedure. The temperature of the room was controlled to be between 20° C. to 22° C. to make sure that all the patients were exposed to the same temperature before applying the cooling stimulus to the area of interest. At the beginning of the procedure, a square registration marker was placed around the lesion with the lesion centered in the opening. A visible image of the lesion was then taken with a digital camera for reference purposes. After collection of the visible image, the subject's skin within the marker opening was cooled for 30 seconds using the cooling unit. After cooling, the exposed area was allowed to warm up naturally to ambient temperature. During the cooling and warm-up phases, thermal images of the skin were captured for a total of two minutes at a rate of 60 frames per second. All the thermal images were recorded using an uncompressed 14-bit format. The total time required to complete the imaging procedure was less than five minutes. If the subject was scheduled for a biopsy, the biopsy was performed following the data collection by the attending dermatologist and sent to pathology for diagnosis. The biopsy results were delivered to us within the next two weeks following the DTI procedure.

Since involuntary movements cannot be avoided, image registration was performed on the sequence of IR images. Moreover, to correctly reference the lesion location in the IR sequence in order to compute the average TRC, the visible picture must also be spatially aligned with respect to the IR sequence; therefore, the visible image was considered as an additional frame for the registration. After the registration, both the visible image and the entire infrared sequence are spatially aligned. As such, the average TRC of each patient can be defined by selecting the boundary of the lesions using the visible image.

The infrared sequence was then radiometrically calibrated using a two-point calibration. The two-point calibration was performed in a frequent manner, to take into account the drift of the camera's gain and offset. Specifically, the study utilized a Mikron M315X blackbody source.

At this stage, the infrared sequence has been spatially aligned by the image registration, the average TRC for the patient was obtained by using the visible image and the radiometric calibration is utilized to convert the TRC into a temperature measurement.

From the 140 subjects, 58 had a malignant condition (including melanoma, basal-cell and squamous-cell carcinoma) and 82 subjects had benign conditions. The subjects were diagnosed by means of excisional biopsies performed at the University of New Mexico Dermatology Clinic, New Mexico, USA. By performing the training over different sizes and permutations of datasets from the 140 patients while testing the method on the remaining patients that where not used in the training, the inventors found that at least 110 patients with known conditions and ten KL coefficients may be used to train the method in order to perfectly separate both benign and malignant conditions for the patient datasets used in the training stage. In order to assess the robustness of using a size of 110 patients in the training dataset and 10 KL coefficients, the inventors repeated the training 200 times, each time with a distinct (but randomly selected) permutation of 110 patients from the totality of 140 patients. Each selection of the 200 training dataset permutations yielded a lesion classifier. The inventors then tested the method by studying the performance of each of the 200 classifiers, namely, the inventors used each classifier to determine the condition of each of the 30 remaining patients (outside of its training dataset). The results demonstrate that some embodiments achieve 100% accuracy (i.e., 100% sensitivity and 100% specificity) for 46% of the 200 training selections, which the inventors term the highly reliable training data-sets. Moreover, the tested embodiment achieves 100% sensitivity and 95% specificity (i.e., 5% false-alarm rate) for 76% of the 200 training datasets, and 100% sensitivity and 90% specificity for 93% of the 200 training datasets. These results demonstrate that by using highly reliable training datasets, the disclosed technique is capable of correctly classifying both benign and malignant skin-cancer conditions with total accuracy. In addition, the inventors have observed variability in the sensitivity within only 3% across the 200 training datasets. Moreover, for different possible lesion boundaries (required to define the pixel-to-pixel averaged TRCs), the inventors observed that the method presents a variability of 0.1% due to a change of 30% in the radius of the selected lesion.

After completing the above study, 11 new patient TRCs with known biopsy results were acquired: by means of biopsies 5 were diagnosed as malignant and 6 as benign. By testing the method on this new set of patients while using the same classifiers that were generated by the 200 training datasets from the previous study, the inventors have correctly identified all malignant lesions and misclassified only one benign lesion for 76% of the original 200 classifiers. Moreover, the inventors were able to correctly classify all new 11 lesions for 36% (71 classifiers) of the original 200 classifiers. Out of these 71 classifiers, 58 were from the "highly reliable dataset" identified in the earlier study (original set of 140 patients) as described in the previous paragraph, and 13 of the 71 were from the data set permutations that misclassified only one benign in the original set of patients. This observation shows consistency in the performance of the classifiers that were trained by the highly reliable datasets.

VI. Variations & Fifteen Example Distinctions from Known Solutions (1) The detection method exploits, in a probabilistic sense, the temporal evolution of the warming-up process, as obtained from the thermal-image sequence, as described herein, to extract statistical features that can be utilized to discriminate a case of a benign lesion from a malignant lesion. The term evolution is emphasized to highlight the importance of the temporal order of the warming-up data obtained from the image sequence. This is why the performance is far better than that obtained when the Euclidean norm of the thermal-image sequence is used because the latter, unlike the proposed method, does not depend on the ordering of the images in the sequence.

(2) The process for obtaining the statistical features may rely on, but is not limited to, theory for optimal detection based on continuous-time stochastic signals, which relies on Mercers Theorem and its corollary of Karhunen-Loève expansion for the autocorrelation function in continuous time.

(3) The success of the process defined in (2) relies on knowledge of the autocorrelation function of the warming-up process under each hypothesis, which has not been known prior to this disclosure to the best of the inventors' knowledge. This disclosure presents the construction of such autocorrelation function by parameterizing the warming-up process using a few random variables, and by estimating (from patient-data) the probability distribution for these random variables and their relevant correlation functions.

(4) To enable the parametric description of the warming-up process, and ultimately estimating its autocorrelation function, the signal model for the warming-up process, as taught herein, is based on the physics of the problem (i.e., solving the heat equation). Of note is that to obtain a mathematical function of time representing the warming-up process for each patient, it suffices to use only the surface temperature as a data entry while the heat equation is solved analytically. Such mathematical function may be parameterized by the aforementioned random variables, and a realization of the set of random variables may be obtained for each patient.

(5) The parameters of the autocorrelation functions (for each hypothesis) can be modeled using a multivariate Gaussian random distribution for which the marginal parameters and correlations can be estimated from the data. Those skilled in the art can utilize different multivariate distributions of the random parameters if further knowledge of the physics of the problem is acquired.

(6) After the Karhunen-Loève theorem is applied to the estimated autocorrelation functions (for each hypothesis), this disclosure shows that ten eigenvalues (one for each of the most important eigenfunctions) may be used to describe the detection problem. If a larger and more diverse dataset is available, those skilled in the art can utilize additional eigenfunctions to improve the performance of the algorithm.

(7) The decision rule that maps the statistical features obtained from the probabilistic-analysis process described in (6), is, but not limited to, that which maximizes the detection probability while keeping the false-alarm rate at a fixed level. This is called a Neyman-Pearson decision rule. However, other decision rules may be applied if other optimality criteria (e.g., Bayesian or minimax criteria) are desired.

(8) The methodology can be further improved by including spatial information of the suspicious lesions. The spatial information may include, but is not limited to, the lesion asymmetry, the lesion border, different colors within the lesion and lesion diameter. The lesion texture (estimated from acquired visible images) can also be included.

(9) The spatial information mentioned in (8) could be, but is not limited to, fused into the detection rule described in (7), or can form a separate decision rule that can be later fused with other decision rules to increase either the detection probability or reduce the false-alarm probability, alter both jointly, or any combination or optimality criteria desired by those skilled in the art.

(10) The spatial information can also be utilized to describe the optimal boundary and therefore size of the lesions in such a way that a multidimensional continuous-time signal is utilized to characterize the warming-up of process for each patient.

(11) The multidimensional continuous-time signal can also be utilized in the algorithm taught in this disclosure in order to improve any optimality criteria desired.

(12) The decision rule in (7) in conjunction with any of the extension described in (8)-(11) can all be fused together or fused in any desired combination such that the fused decision-making stage allow the expert to improve any desired optimality criteria.

(13) Even though an embodiment is explained herein for the case of two hypotheses (i.e., detection of benign versus malignant lesions) it can be easily extended to any number of hypotheses that may include, but not be limited to, different type of benign or malignant cases.

(14) Some types of benign cases mentioned in (13) may include, but are not limited to, dysplastic nevus, papular benign skin lesions and macular benign skin lesions.

(15) Some types of malignant cases mentioned in (13) may include, but is not limited to, malignant melanomas, basal-cell carcinomas and squamous-cell carcinomas.

VII. Example Technical Details and Hardware

This section elaborates on and fleshes out some of the techniques disclosed above.

a. Formulation of the Detection Problem

The skin-cancer-detection technique according to some embodiments is based on the following physical principle. Skin cancers, like all solid malignant tumors, require a blood supply in order to grow larger than a few millimeters in diameter. To achieve this, tumors induce the growth of new capillary blood vessels (a process called angiogenesis) by producing specific angiogenesis-promoting growth factors. Even at an early stage, the so-called precancerous lesions of the skin, including atypical moles, are already angiogenic, as indicated by their higher density of capillaries than surrounding normal skin. As the tumor develops from precancerous skin lesions to full-blown skin cancer, new blood-vessel growth continues. The skin-cancer-detection technique according to some embodiments is based on the premise that the presence of new blood vessels and the increased blood supply should somewhat change the thermal response of the tumor when a stimulus is applied in comparison with the thermal response of healthy tissue.

Under this scenario, some embodiment utilize the assumption that the patient condition is hidden within the TRC of a suspicious lesion. Moreover, the malignancy of a lesion can be inferred only by studying the mole, i.e., the area of the skin which has tissue of a different color as compared with the rest of the surrounding skin. Thus, denote S(t) as the average TRCs (across all the pixels within the area of the mole) of patients with benign and malignant condition, respectively. The binary detection problem of detecting if a measured TRC, Y(t), belongs to a patient with benign (null hypothesis, $H_0$) or malignant (alternative hypothesis, $H_1$) condition is formulated by the hypothesis-testing problem $H_0: Y(t)=S(t;\Theta_0)$, $0 \leq t \leq T$ versus $H_1: Y(t)=S(t;\Theta_1)$, $0 \leq t \leq T$, where T represents the acquisition time and $\Theta_j$ represents the random parameters that characterize the TRC under the j-th hypothesis, with j=0, 1. (Some embodiments may include the melanoma and non-melanoma conditions, i.e., basal-cell and squamous-cell carcinomas, in the alternative hypothesis $H_1$ at this stage.) The continuous-time signals $S(t;\Theta_j)$, for j=0, 1 may be modeled as stochastic processes due to the nature of the problem, the unknown quantities and the patient-specific parameters that cannot be determined a priori, as described next.

b. Temperature Model

The following subsections describe in part block 108 of FIG. 1.

According to some embodiments, the mathematical model for skin temperature may incorporate detailed physical and statistical information about the TRC signals, and it may be simple enough to ensure a feasible solution with the available information. The model may be motivated by the physical mechanisms that generate the TRCs. First, some embodiments are based on measuring the temperature of the surface of the skin, which is governed by the thermal properties of the subcutaneous tissue and the surroundings. Thus, some embodiments assume that the physics of the problem is described by a heat equation, which characterizes the spatio-temporal thermal response of the human skin. Second, it is believed that the veins in the fat-dermis layer and the blood vessels within the dermis layer are the most relevant source of heat acquired by the infrared camera. Moreover, there is no evidence that, using an infrared camera, subcutaneous thermal processes beyond such an interface can be resolved. Third, there is evidence that suggests that the in-vivo emissivity of the skin is near unity. Therefore, some embodiments assume that the skin mimics a perfect blackbody source, meaning that the skin is assumed to be a perfect emitter and that all the subcutaneous thermal processes are integrated to the surface of the skin. As a consequence, the temperature of the skin captures the cumulative effect of all the subcutaneous thermal processes, which allows for a definition of an effective diffusion constant, $\mathcal{D}$, that consolidates all the skin thermal parameters (i.e., the effective tissue density, $\rho$, the effective specific heat of the tissue, C, and the effective thermal conductivity, k).

As stated herein, some embodiments consider the average TRC for each lesion, which implies that the model will be affected only by the variations on the depth of the lesion, namely, in the x direction. Therefore, the temperature of the skin sample may be modeled by the one-dimensional heat equation, $$\rho C \frac{\partial u}{\partial t} = k \frac{\partial^2 u}{\partial x^2}, \quad \begin{array}{l} t \in [0, T] \\ x \in [0, H] \end{array},$$

where T is the acquisition time and H the bottom of the spatial domain. (To clarify, x=0 represents the skin surface.) The effective diffusion constant, $\mathcal{D}$, may be defined by $k/\rho C$.

Since it is difficult or intractable to resolve the temperature beyond the fat-dermis interface because of the veins (that carry blood at a temperature determined by the core of the human body), some embodiments set the bottom of the spatial domain to be at the fat-dermis interface, meaning that H may be given by the sum of the thicknesses of the epidermis and dermis layers. The bottom of the spatial domain is in contact with the veins of the fat-dermis interface and zones with a high density of blood vessels and, thus, some embodiments assume that it is at a constant temperature, termed the blood or core temperature, $T_B$, for all time. This defines the first boundary condition: $u(H,t)=T_B$.

Some embodiments, including the study that led to the experimental results described herein, perform the initial cooling of the lesion and acquire the subsequent thermal recovery. Right after the cooling is stopped the surface of the skin is exposed to the natural convection with the surrounding air. Therefore, the heat flux at the surface, $q''=-k\, u_x(0,t)$, is equal to the product of the convective heat transfer coefficient, $h_\infty$, and the temperature difference between the skin surface, $u(0,t)$, and the temperature of the air, $T_A$, i.e., $-k\, u_x(0,t)=h_\infty(u(0,t)-T_A)$.

In summary, the model for the temperature may be given by $$\frac{\partial u}{\partial t} = \mathcal{D}\frac{\partial^2 u}{\partial x^2}, \quad \begin{array}{l} t \in [0,T] \\ x \in [0,H] \end{array}$$

$$q'' = -ku_x(0,t) = h_\infty(u(0,t) - T_A),$$

$$u(H,t) = T_B,$$

$$u_x(H,t) = 0,$$

where, for convenience, an additional boundary condition over the heat-flux at the bottom of the chunk of skin is included. This partial differential equation (PDE) may be solved by dividing the temperature model, $u(x,t)$, into the steady-state solution, $u_{ss}(x)$, and the transient solution, $v(x,t)$.

c. Steady-State Solution

The steady-state solution can be found by setting $u_t(x,t)=0$. Therefore some embodiments solve $u_{xx}=0$, which has a solution of the form $u_{ss}(x)=Ax+B$. Using the bottom boundary conditions, obtain $u_{ss}(H)=AH+B=T_B$, or $B=T_B-AH$. Replacing into the top boundary condition results in $A=(h_\infty/k)(T_B-T_A)/(Hh_\infty/k-1)$ and $B=(T_B-(Hh_\infty/k)T_A)/(1-Hh_\infty/k)$. Then, the steady-state solution may be represented by, for example:

$$u_{ss}(x) = \left(\frac{\frac{h_\infty}{k}(T_B - T_A)}{\frac{h_\infty H}{k} - 1}\right)x + \left(\frac{T_B - \frac{h_\infty H}{k}T_A}{1 - \frac{h_\infty h}{k}}\right), x \in [0, H].$$

d. Transient Solution

The transient solution, $v(x,t)$, also satisfies the heat equation model, but the boundary conditions are different because of the steady-state solution already computed. The modified boundary conditions are, for example:

$h_\infty v(0,t)+kv_x(0,t)=0$, $v(H,t)=0$, $v_x(H,t)=0$.

The solution is obtained by following the separation of variables approach, i.e., we assume that the transient solution can be defined as the product of two functions: $v(x,t)=X(x)T(t)$, transforming the transient equation to two ordinary differential equations, for example $X''(x)-\alpha X(x)=0$, $x \in [0,H]$, $\dot{T}(t)-\alpha \mathcal{D} T(t)=0$, $t \in [0,T]$, where $\alpha$ is known as the separation constant. The space ODE may be solved first and the solutions associated with the separation constant $\alpha$ may be found next. In particular, there are three cases of interest: $\alpha=0$, a positive and a negative. On one hand, it can be easily demonstrated that $\alpha \geq 0$ only leads to the trivial solution. For a negative, on the other hand, the non-trivial solution is achieved if, for $\alpha=-\mu^2$, $\mu$ satisfies the trigonometric equation:

$$\tan\mu H = \frac{k}{h_\infty}\mu.$$

Given the periodicity of this equation, there will be infinite solutions $0<\mu_1<\mu_2<\ldots$. For each solution to this equation, $\mu_n$, there is an associated solution to the ODE, for example:

$$X_n(x) = C_n\cos\mu_n x + D_n\sin\mu_n x, \quad \begin{array}{l} x \in [0, H] \\ n = 1, 2, \ldots \end{array},$$

with a corresponding solution for the time ODE $T_n(t)=\exp(-\mathcal{D}\mu_n^2 t)$, $n=1, 2, \ldots$. Thus, the transient solution is the superposition of each one of the nth transient solutions $v_n(x,t)=X_n(x)T_n(t)$, e.g., $$v(x,t) = \sum_{n=1}^{\infty}(C_n\cos\mu_n x + D_n\sin\mu_n x)e^{-\mathcal{D}\mu_n^2 t},$$

$x \in [0, H]$ $t \in [0, T]$.

The coefficients $C_n$ and $D_n$ may be determined to match the generalized Fourier-series expansion of the initial condition function minus the steady-state solution. Some embodiments utilize the solution at the skin surface, because that is the temperature the infrared camera measures. When evaluated at the surface, the temperature model becomes, e.g.:

$$u(0,t) = \left(\frac{T_B - \frac{h_\infty H}{k}T_A}{1 - \frac{h_\infty H}{k}}\right) + \sum_{n=1}^{N}C_n e^{-\mathcal{D}\mu_n^2 t},$$

where N is the minimum number of exponentials required to accurately model the TRCs. Given the lack of knowledge regarding the initial temperature profile for the subcutaneous layers of the skin, it may not be possible to know a priori the initial condition function required to compute these coefficients and, thus, the appropriate value of N. This problem may be addressed by utilizing different test functions as initial conditions and numerically studying the decay of the coefficients $C_n$. According to some embodiments, two exponential functions plus a constant may be sufficient to model the TRCs.

e. Probabilistic Model for the TRC

Although the mathematical model is based on the physics of the problem, it utilizes the precise knowledge of parameters that are patient-specific and, in general, unknown (e.g., the air temperature, the blood temperature, the precise location of the fat-dermis interface, to name a few). To address this issue, some embodiments construct the physical model by assuming that the analytical solution of the heat equation provides the mathematical structure of the model, and by parameterizing this structure with random parameters that must be estimated from the data. Hence, the TRC under the jth hypothesis may be modeled by, for example:

$$S(t;\Theta_j)=\theta_{j,1}+\theta_{j,2}e^{-\theta_{j,3}t}+\theta_{j,4}e^{-\theta_{j,5}t}$$

where $\Theta_j$ is a random vector of parameters for the jth hypothesis (j=0, 1).

In order to estimate the distribution of the random parameters under each hypothesis, patients with a known condition are utilized. (Biopsy results may be considered as the ground truth.) Each pixel within the pigmented area of a patient lesion with known diagnosis will generate a realization of these random parameters. With a sufficient number of patients with known conditions, some embodiments can obtain the histograms of these realizations, which, in turn, allow for estimating the statistical distributions of the parameters.

f. Solution to the Detection Problem: Autocorrelation Functions and Mercer's Theorem Some embodiments may solve the detection problem by, with the ACFs under each hypothesis at hand, first reducing the continuous-time TRCs to an equivalent discrete-time set by means of Mercer's theorem (block 116 of FIG. 1) in conjunction with the Karhunen-Loève (KL) expansion (block 120 of FIG. 1). After the expansion, the solution of the continuous-time problem may be performed in discrete-time as a function of the KL coefficients.

The ACF may be a measure of similarity (i.e., statistical correlation) between a stochastic process and a time-shifted copy of itself. Provided that the stochastic processes are assumed to have zero-mean, the autocovariance and autocorrelation functions coincide, where the latter for the jth hypothesis is defined by $R_j(t,u)=E[S(t;\Theta_j)S(u;\Theta_j)]$, where E denotes expectation.

By replacing the TRC stochastic model the ACF associated with the jth hypothesis is, for example:

$$\begin{aligned}R_j(t,u) &= E[S(t;\Theta_j)S(u;\Theta_j)] \\ &= E[(\theta_{j,1}+\theta_{j,2}e^{-\theta_{j,3}t}+\theta_{j,4}e^{-\theta_{j,5}t})(\theta_{j,1}+\theta_{j,2}e^{-\theta_{j,3}u}+\theta_{j,4}e^{-\theta_{j,5}u})] \\ &= E[\theta_{j,1}^2]+E[\theta_{j,1}\theta_{j,2}e^{-\theta_{j,3}u}]+E[\theta_{j,1}\theta_{j,4}e^{-\theta_{j,5}u}]+ \\ &\quad E[\theta_{j,1}\theta_{j,2}e^{-\theta_{j,3}t}]+E[\theta_{j,2}^2e^{-\theta_{j,3}(t+u)}]+E[\theta_{j,2}\theta_{j,4}e^{-\theta_{j,3}t}e^{-\theta_{j,3}u}]+ \\ &\quad E[\theta_{j,1}\theta_{j,4}e^{-\theta_{j,3}t}]+E[\theta_{j,2}\theta_{j,4}e^{-\theta_{j,5}t}e^{-\theta_{j,3}u}]+E[\theta_{j,4}^2e^{-\theta_{j,5}(t+u)}],\end{aligned}$$

for $0\leq t$, $u\leq T$. It can be observed from this equation that computing the expectation of the product of random variables may precede computing the analytical ACF. The inventors have determined some formulas that allow for expressing each expectation of the product of random variables as a function of pairwise covariance between the parameters. For example, the first term in the ACF formulae is the expectation of two random variables, which is known to be equal to $E[XY]=E[X]E[Y]+\text{cov}(X, Y)$; therefore, $E[\theta_{j,1}^2]=E[\theta_{j,1}]^2+\text{var}(\theta_{j,1})$, which is the sum of two moments that can be estimated from patient data with known diagnosis. The second term is the product of two random variables and a function of a random variable, which is also a random variable but indexed by a continuous parameter t. The inventors have determined that the expectation of the product of these three random variables may be computed by, for example:

$$E[XUV]=E[X]E[U]E[V]+E[X]\text{cov}(U,V)+E[U]\text{cov}(X,V)+E[V]\text{cov}(X,U)$$

where it is assumed that the random variables can be approximated as Gaussian random variables. Thus, the second term in the ACF formulae can be computed as, for example:

$$\begin{aligned}E[\theta_{j,1}\theta_{j,2}e^{-\theta_{j,3}u}]&=E[\theta_{j,1}]E[\theta_{j,2}]E[e^{-\theta_{j,3}u}]+E[\theta_{j,1}]\\ &\quad\text{cov}(\theta_{j,2},e^{-\theta_{j,3}u})+E[\theta_{j,2}]\text{cov}(\theta_{j,1},e^{-\theta_{j,3}u})+E[e^{-\theta_{j,3}u}]\\ &\quad\text{cov}(\theta_{j,1},\theta_{j,2}).\end{aligned}$$

where the mean of the exponential function is, for example:

$$E[e^{-\theta_{j,3}u}]=\exp\left[-uE[\theta_{j,3}]+u^2\frac{\text{var}[\theta_{j,3}]}{2}\right]$$

and the pairwise covariance of the form $\text{cov}(\theta_{j,k}, e^{-\theta_{j,3}u})$ is the covariance of a Normal-Lognormal distributed random variable. (The random variable Z is said to follow a Normal-Lognormal (NLN) distribution if $Z=Xe^Y$, where the two random variables X and Y are jointly Gaussian random variables.) The of the NLN-distributed random variable is, for example:

$$\text{cov}(\theta_{j,k}, e^{-\theta_{j,3}u})=\rho_{k,3}\sigma_{j,k}u\sigma_{j,3}\exp\left[-u\mu_{j,3}+u^2\frac{\sigma_{j,3}^2}{2}\right]$$

where $\rho_{k,3}$ is the estimated correlation coefficient between $\theta_{j,k}$ and $\ln\theta_{j,3}$. Substituting everything back into the equation for the second term of the ACF produces $$\begin{aligned}&E[\theta_{j,1}\theta_{j,2}e^{-\theta_{j,3}u}]= \\ &\mu_{j,1}\mu_{j,2}\exp\left[-u\mu_{j,3}+u^2\frac{\sigma_{j,3}^2}{2}\right]+\mu_{j,1}\rho_{2,3}\sigma_{j,2}u\sigma_{j,3}\exp\left[-u\mu_{j,3}+u^2\frac{\sigma_{j,3}^2}{2}\right]+ \\ &\mu_{j,2}\rho_{1,3}\sigma_{j,1}u\sigma_{j,3}\exp\left[-u\mu_{j,3}+u^2\frac{\sigma_{j,3}^2}{2}\right]+ \\ &\text{cov}(\theta_{j,1},\theta_{j,2})\exp\left[-u\mu_{j,3}+u^2\frac{\sigma_{j,3}^2}{2}\right],\end{aligned}$$

The mathematical expression to compute the second term in the ACF uses an estimation of the mean and variance of each random variable in the expression as well as the covariance between some pairs of random variables. The inventors utilized patient data with known diagnosis and the stochastic model to estimate these moments. First, for each patient the inventors performed the nonlinear least-square fitting of the patient TRC with the parameterized stochastic model. Second, the inventors assumed that the fitting of each TRC gives a realization of each random variable, so they utilized the fitting parameters to estimate each of the required moments. The inventors also utilized the same method to estimate the moments required for the other terms that we discuss next.

Using the same rationale, the third term can be expressed as, for example:

$$\begin{aligned}&E[\theta_{j,1}\theta_{j,4}e^{-\theta_{j,5}u}]= \\ &\mu_{j,1}\mu_{j,4}\exp\left[-u\mu_{j,5}+u^2\frac{\sigma_{j,5}^2}{2}\right]+\mu_{j,3}\rho_{4,5}\sigma_{j,4}u\sigma_{j,5}\exp\left[-u\mu_{j,5}+u^2\frac{\sigma_{j,5}^2}{2}\right]+\end{aligned}$$

-continued $$\mu_{j,4}\rho_{1,5}\sigma_{j,1}u\sigma_{j,5}\exp\left[-u\mu_{j,5}+u^2\frac{\sigma_{j,5}^2}{2}\right]+$$

$$\text{cov}(\theta_{j,1},\theta_{j,4})\exp\left[-u\mu_{j,5}+u^2\frac{\sigma_{j,5}^2}{2}\right].$$

Similarly, the inventors expressed the fourth, fifth, seventh and ninth terms that define the ACF by simply interchanging the random variables accordingly.

The sixth and eighth terms have the expectation of the product of four random variables, for example:

$$E[XYUV] = E[X]E[Y]\text{cov}(U,V) + E[X]E[U]\text{cov}(Y,V) +$$
$$E[X]E[V]\text{cov}(Y,U) + E[Y]E[U]\text{cov}(X,V) + E[Y]E[V]\text{cov}(X,U) +$$
$$E[U]E[V]\text{cov}(X,Y) + \text{cov}(X,Y)\text{cov}(U,V) +$$
$$\text{cov}(X,U)\text{cov}(Y,V) + \text{cov}(X,V)\text{cov}(Y,U) + E[X]E[Y]E[U]E[V].$$

Applying this formulae to the sixth term obtains, for example:

$$E[\theta_{j,2}e^{-\theta_{j,3}t}\theta_{j,4}e^{-\theta_{j,5}u}] =$$

$$\mu_{j,2}\exp\left[-t\mu_{j,3}+t^2\frac{\sigma_{j,3}^2}{2}\right]\text{cov}(\theta_{j,4},e^{-\theta_{j,5}u}) + \mu_{j,2}\mu_{j,4}\text{cov}(e^{-\theta_{j,3}t},e^{-\theta_{j,5}u}) +$$

$$\mu_{j,2}\exp\left[-u\mu_{j,5}+u^2\frac{\sigma_{j,5}^2}{2}\right]\text{cov}(e^{-\theta_{j,5}t},\theta_{j,4}) +$$

$$\mu_{j,4}\exp\left[-t\mu_{j,3}+t^2\frac{\sigma_{j,3}^2}{2}\right]\text{cov}(\theta_{j,2},e^{-\theta_{j,5}u}) +$$

$$\exp\left[-t\mu_{j,3}+t^2\frac{\sigma_{j,3}^2}{2}\right]\exp\left[-u\mu_{j,5}+u^2\frac{\sigma_{j,5}^2}{2}\right]\text{cov}(\theta_{j,2},\theta_{j,4}) +$$

$$\mu_{j,4}\exp\left[-u\mu_{j,5}+u^2\frac{\sigma_{j,5}^2}{2}\right]\text{cov}(\theta_{j,2}e^{-\theta_{j,5}t}) +$$

$$\text{cov}(\theta_{j,2},e^{-\theta_{j,3}t})\text{cov}(\theta_{j,4},e^{-\theta_{j,5}u}) +$$

$$\text{cov}(\theta_{j,2},\theta_{j,4})\text{cov}(e^{-\theta_{j,3}t},e^{-\theta_{j,5}u}) + \text{cov}(\theta_{j,2},e^{-\theta_{j,5}u})\text{cov}(e^{-\theta_{j,3}t},\theta_{j,4}) +$$

$$\mu_{j,2}\exp\left[-t\mu_{j,3}+t^2\frac{\sigma_{j,3}^2}{2}\right]\mu_{j,4}\exp\left[-u\mu_{j,5}+u^2\frac{\sigma_{j,5}^2}{2}\right].$$

This equation uses the estimation of means and covariance between a pair of random variables that were already defined for the previous terms except for the covariance $\text{cov}(e^{-\theta_{j,3}t}, e^{-\theta_{j,5}u})$, which is the covariance of two Log-Normal distributed random variables. It is known that this covariance can be approximated by, for example:

$$\text{cov}(e^{-\theta_{j,3}t}, e^{-\theta_{j,5}u}) = E[e^{-\theta_{j,3}t}]E[e^{-\theta_{j,5}u}](e^{\text{cov}(\theta_{j,3},\theta_{j,5})} - 1)$$

$$= \exp\left[-t\mu_{j,3}+t^2\frac{\sigma_{j,3}^2}{2}\right]\exp\left[-u\mu_{j,5}+u^2\frac{\sigma_{j,5}^2}{2}\right](e^{\text{cov}(\theta_{j,3},\theta_{j,5})} - 1)$$

which again uses the estimation of the mean, variances and covariance between the random variables. The same mathematical expression can be utilized for the other covariance with the same mathematical structure present in the expression of the sixth term. The eighth term may be estimated using the same formulae while replacing the corresponding random variables as required.

For each term, the inventors have estimated the required moments from patient data with known diagnosis and added up the resulting mathematical expressions in order to analytically estimate the ACF. Both estimated ACFs 602, 604 are shown in FIG. 6.

Because the processes are zero-mean, the ACFs are also the covariance functions, which means they are symmetric and nonnegative definite. As a consequence, every eigenvalue obtained by an integral equation, for example:

$$\lambda_{j,k}\phi_{j,k}(t) = \int_0^T R_j(t,u)\phi_{j,k}(u)du, \ j=0,1$$

is greater than zero, for k=1, 2, . . . . The ACF $R_j(t,u)$ is called the kernel of the integral equation, and under the assumption that the processes have finite mean-square value, i.e., $E[S_j(t;\Theta_j)]<\infty$, then the covariance function satisfy the restriction $\iint R_j^2(t,u) \, dt \, du < \infty$ for $0 \leq t, u \leq T$, where T is a finite number. These restrictions yield some properties such as, (1) there exists at least one square-integrable function $\phi_{j,k}(t)$ for each j=0, 1 and a real number $\lambda_{j,k} \neq 0$ that satisfy the integral equation; (2) the eigenfunctions corresponding to different eigenvalues are orthogonal; (3) there is at most a countably infinite set of eigenvalues and all are bounded, to name a few. Of note is the property that because $R_j(t,u)$, for j=0, 1 are nonnegative definite functions, they can be expanded in the uniform convergent series (for $0 \leq t, u \leq T$)

$$R_j(t,u) = \sum_{k=1}^{\infty} \lambda_{j,k}\phi_{j,k}(t)\phi_{j,k}(u)$$

which is known as Mercer's theorem (see block 116 of FIG. 1). Mercer's theorem is a continuous analog of the singular-value or eigenvalue decomposition of a symmetric positive definite matrix. One of its applications is to find convenient ways to express stochastic processes, via the Karhunen-Loève expansion (block 120 of FIG. 1), which is presented next.

g. Karhunen-Loève Expansion

The Karhunen-Loève (KL) expansion (block 120 of FIG. 1) can be seen as a generalization of the singular-value decomposition (SVD) of a matrix, which can be written as a sum of outer products of vectors. A number of SVD results have an analog in the KL expansion, being the most notable that the KL expansion is a particularly suitable approximation of the process (because it minimizes the mean-square error with respect to the original process) when the expansion is truncated to consider only the first eigenvalues, arranged in decreasing order. Thus, the KL expansion allows for representing (in the mean-square sense) the TRCs under each hypothesis by the convergent series that may be represented as, for example:

$$S(t;\Theta_j) = \sum_{k=0}^{\infty} S_{j,k}\phi_{j,k}(t), \; j = 0, 1$$

$$Z = \sum_{k=1}^{K} \left(\frac{Y_{0,k}^2}{\lambda_{0,k}} - \frac{Y_{1,k}^2}{\lambda_{1,k}}\right) \underset{H_0}{\overset{H_1}{\gtreqless}} \eta.$$

where the coefficients $S_{0,k}$ and $S_{1,k}$ (termed the KL coefficients) are the projection of the TRCs onto the eigenfunctions $\phi_{0,k}(t)$ and $\phi_{1,k}(t)$, respectively. The KL coefficients in the expansion are uncorrelated random variables that contain all the statistical information from the TRCs, whereas the eigenfunctions embody all the time variations of the TRCs. As a consequence, the KL coefficients can be seen as a statistical equivalent representation of the TRCs. With such statistical equivalence between a TRC and its KL sequence, some embodiments can employ optimal-inference theory to announce the hypothesis based on the KL coefficients of an observed TRC. A procedure for doing so is to construct the likelihood ratio associated with the equivalent KL representation, as described in the next subsection.

h. Likelihood Ratio

After applying the KL expansion to the random processes under each hypothesis, the statistically equivalent detection problem correspond to classifying an incoming average TRC, Y(t), represented by its KL coefficients, for example:

$$Y_{j,k} = \int_0^T Y(t)\phi_{j,k}(t)dt$$

for j=0, 1 and k=1, 2, . . . as belonging to either $H_0$ or $H_1$. One approach to address this problem is to construct the likelihood ratio (LR) of the random KL coefficients, compare it with an optimally-defined threshold, and decide if Y(t) belongs either to $H_0$ or $H_1$.

The LR may be defined as $L(Y)=p_1(Y)/p_0(Y)$, where the vector Y stands for all the KL coefficients of the TRC Y(t). The construction of the likelihood ratio uses the joint distribution of each set of KL coefficient under each hypothesis. This problem may be solved by assuming that the stochastic processes are Gaussian random processes. This assumption leads to Gaussian KL coefficients, and, since the KL coefficients are uncorrelated, they will also be independent. Under this scenario, the logarithm of the likelihood ratio (LR) is represented as, for example:

$$\log L(Y) = \frac{1}{2}\sum_{k=1}^{\infty} \log\left(\frac{\lambda_{0,k}}{\lambda_{1,k}}\right) + \frac{1}{2}\sum_{k=1}^{\infty} \left(\frac{Y_{0,k}^2}{\lambda_{0,k}} - \frac{Y_{1,k}^2}{\lambda_{1,k}}\right).$$

The LR can be compared with a threshold in order to make a decision, a process called the likelihood ratio test (LRT). It is possible to reduce the LR mathematical definition to the terms that directly depend on the input signal's KL coefficients. This reduction defines the test-statistic, which compactly contains all the statistical information regarding the signal's KL coefficients. As such, the test-statistic is compared to a decision threshold, $\eta$ (the next subsection explains how to optimally define such a threshold). According to some embodiments, test-statistic is given by the random variable represented as, for example:

i. Optimal Decision Rule

This subsection describes block 124 of FIG. 1. The Neyman-Pearson (NP) lemma states that if the threshold $\eta>0$ is chosen such that the false-alarm probability is at a fixed level, say $\alpha$, then the LRT is the most powerful test. In other words, in some embodiments, the LRT will provide the maximum achievable detection probability such that the false-alarm probability is equal or less than an arbitrarily prescribed level $\alpha$.

The LRT uses the distribution, under each hypothesis, of the test statistics Z. It turns out that the test-statistic is a linear combination of chi-square random variables with a different set of coefficients under each hypothesis. In symbols, $Z=\sum_{k=1}^{\infty} a_k X_k$, where the coefficients are given by, for example:

$$a_k = \begin{cases} \left(1 - \frac{\lambda_{0,k}}{\lambda_{1,k}}\right), & H_0 \\ \left(\frac{\lambda_{1,k}}{\lambda_{0,k}} - 1\right), & H_1 \end{cases}$$

When a finite number of eigenvalues are used to define the test-statistic, the distribution of the statistics under each hypothesis can be approximated by the distribution of a quadratic form of a Gaussian distributed random variable. An absolutely convergent series that defines the cumulative distribution function (CDF) of such a linear combination may be employed. The theoretical performance of the NP decision rule can be obtained by utilizing this formula and the definitions of the false-alarm and detection probabilities. Since the CDF formula uses a finite linear combination, the inventors consider the change in the theoretical performance as we increase the number of eigenvalues (sorted in decreasing order). The result of this study is shown in FIG. 2, where for different number of eigenvalues, FIG. 2 depicts the false-alarm probability versus the detection probability—a plot known as receiver-operating characteristic (ROC) curve of the detector. As expected, more eigenvalue-eigenfunction pairs are included, more features are extracted from the TRC and the theoretical performance is improved, plateauing at a level, at the 12th eigenvalue-eigenfunction pair.

j. Determining the Optimal Number of KL Coefficients

This subsection describes block 122 of FIG. 1. A metric to compare the ROC curves of two classifiers is the area under the ROC curve (AUC). The Table below shows the AUC of the ROC curves shown in FIG. 2. A rule-of-thumb to evaluate the performance of a classifier states that a classifier has excellent performance if the AUC is >0.90. (A perfect classifier has an AUC equal to unity.)

TABLE

Area under the ROC curve (AUC) as the number of distinct eigenvalue-eigenfunction pairs (K) is increased

| K | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| AUC | 0.50 | 0.56 | 0.67 | 0.72 | 0.76 | 0.81 | 0.83 | 0.84 | 0.85 | 0.90 | 0.96 | 0.98 | 0.98 | 0.98 | 0.98 |

As a consequence, some embodiments will present excellent classification when at least ten eigenvalue-eigenfunction pairs are used (i.e., when K≥10) and the performance according to some embodiments may plateau when twelve eigenvalue-eigenfunction pairs are utilized. (As discovered in the cohort study described herein, some embodiments can achieve perfect classification when ten eigenvalue-eigenfunction pairs are utilized.)

Once the desired false-alarm probability is defined, say 0.05 (i.e., a specificity of 95%), some embodiments use the number of eigenvalue-eigenfunction pairs, e.g., K=10, in order to achieve excellent performance, and determine the optimum decision threshold that yields such a false-alarm probability for that number of eigenvalue-eigenfunction pairs. Once the number of coefficients and the associated decision threshold for the NP decision rule have been determined, this completes the training stage of the hypothesis tester.

Figure 9:
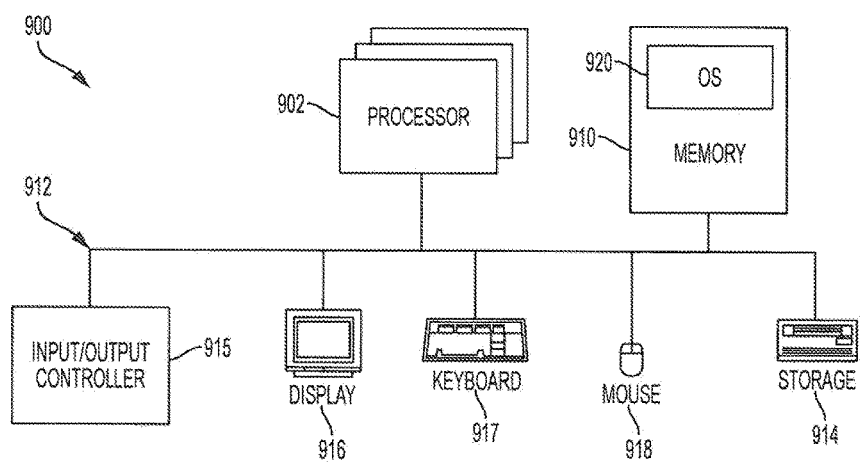
FIG. 9 is an example computer system for performing the disclosed embodiments, consistent with various embodiments.

FIG. 9 illustrates a computer system 900 that is consistent with embodiments of the present disclosure. In general, embodiments of a cancer detection system (e.g., a system performing a method as shown in FIG. 1) or one or more modules therein may be implemented in various computer systems, such as a personal computer, a server, a workstation, an embedded system, a multifunction device, or a combination thereof. Certain embodiments of the cancer detection system may be embedded as a computer program. The computer program may exist in a variety of forms both active and inactive. For example, the computer program can exist as software program(s) comprised of program instructions in source code, object code, executable code or other formats; firmware program(s); or hardware description language ("HDL") files. Any of the above can be embodied on a computer readable medium, which include storage devices and signals, in compressed or uncompressed form. However, for purposes of explanation, system 900 is shown as a general purpose computer that is well known to those skilled in the art. Examples of the components that may be included in system 900 will now be described.

As shown, system 900 may include at least one processor 902, a keyboard 917, a pointing device 918 (e.g., a mouse, a touchpad, and the like), a display 916, main memory 910, an input/output controller 915, and a storage device 914. Storage device 914 can comprise, for example, RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. A copy of the computer program embodiment of the measurement system or modules therein can be stored on, for example, storage device 914. System 900 may also be provided with additional input/output devices, such as a printer (not shown). The various components of system 900 communicate through a system bus 912 or similar architecture. In addition, system 900 may include an operating system (OS) 920 that resides in memory 910 during operation. One skilled in the art will recognize that system 900 may include multiple processors 902. For example, system 900 may include multiple copies of the same processor. Alternatively, system 900 may include a heterogeneous mix of various types of processors. For example, system 900 may use one processor as a primary processor and other processors as co-processors. For another example, system 900 may include one or more multi-core processors and one or more single core processors. Thus, system 900 may include any number of execution cores across a set of processors (e.g., processor 902). As to keyboard 917, pointing device 918, and display 916, these components may be implemented using components that are well known to those skilled in the art. One skilled in the art will also recognize that other components and peripherals may be included in system 900.

Main memory 910 serves as a primary storage area of system 900 and holds data that is actively used by applications, such as the controller and/or the image analyzer in the measurement system, running on processor 902. One skilled in the art will recognize that applications are software programs that each contains a set of computer instructions for instructing system 900 to perform a set of specific tasks during runtime, and that the term "applications" may be used interchangeably with application software, application programs, device drivers, and/or programs in accordance with embodiments of the present teachings. Memory 910 may be implemented as a random access memory or other forms of memory as described below, which are well known to those skilled in the art.

OS 920 is an integrated collection of routines and instructions that are responsible for the direct control and management of hardware in system 900 and system operations. Additionally, OS 920 provides a foundation upon which to run application software and device drivers. For example, OS 920 may perform services, such as resource allocation, scheduling, input/output control, and memory management. OS 920 may be predominantly software, but may also contain partial or complete hardware implementations and firmware. Well known examples of operating systems that are consistent with the principles of the present teachings include MICROSOFT WINDOWS (e.g., WINDOWS CE, WINDOWS NT, WINDOWS 2000, WINDOWS XP, and WINDOWS VISTA), MAC OS, LINUX, UNIX, ORACLE SOLARIS, OPEN VMS, and IBM AIX.

The foregoing description is illustrative, and variations in configuration and implementation may occur to persons skilled in the art. For instance, the various illustrative logics, logical blocks, modules, and circuits described in connection with the embodiments disclosed herein may be implemented or performed with a general purpose processor (e.g., processor 902), a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions described may be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

If implemented in software, the functions may be stored on or transmitted over a computer-readable medium as one or more instructions or code. Computer-readable media includes both tangible, non-transitory computer storage media and communication media including any medium that facilitates transfer of a computer program from one place to another. A storage media may be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

Resources described as singular or integrated can in one embodiment be plural or distributed, and resources described as multiple or distributed can in embodiments be combined. The scope of the present teachings is accordingly intended to be limited only by the following claims. Although the invention has been described with respect to specific embodiments, it will be appreciated that the invention is intended to cover all modifications and equivalents within the scope of the following claims.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

While the present disclosure have been illustrated with respect to one or more implementations, alterations and/or modifications can be made to the illustrated examples without departing from the spirit and scope of the appended claims. For example, it will be appreciated that while the process is described as a series of acts or events, the present disclosure are not limited by the ordering of such acts or events. Some acts may occur in different orders and/or concurrently with other acts or events apart from those described herein. Also, not all process stages may be required to implement a methodology in accordance with one or more aspects or embodiments of the present disclosure. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "conformal" describes a coating material in which angles of the underlying material are preserved by the conformal material. The term "about" indicates that the value listed may be somewhat altered, as long as the alteration does not result in nonconformance of the process or structure to the illustrated embodiment. Finally, "exemplary" indicates the description is used as an example, rather than implying that it is an ideal. Other embodiments of the present disclosure will be apparent to those skilled in the art from consideration of the specification and practice of the disclosure herein. It is intended that the specification and examples be considered as exemplary only, with a true scope and spirit of the present disclosure being indicated by the following claims.

Terms of relative position as used in this application are defined based on a plane parallel to the conventional plane or working surface of a workpiece, regardless of the orientation of the workpiece. The term "horizontal" or "lateral" as used in this application is defined as a plane parallel to the conventional plane or working surface of a workpiece, regardless of the orientation of the workpiece. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the workpiece, regardless of the orientation of the workpiece.

The invention claimed is:

1. A method for classifying lesions, comprising:
cooling an area of skin comprising a lesion of a patient to initiate a warm-up process of the area of skin to an ambient temperature;
receiving a temporal sequence of thermal images of the area of skin representing a thermal recovery of the area of skin, the temporal sequence of thermal images generated by an infrared camera;
generating a temporal profile of the thermal recovery based on the temporal sequence of thermal images;
analyzing temporal statistical properties of the temporal profile;
determining a malignancy probability that the lesion is malignant based on an analysis of the temporal profile, wherein the determining comprises extracting one or more statistical features based on continuous-time stochastic signals in the sequence of thermal images; and
classifying the lesion based on the malignancy probability.

2. The method of claim 1, wherein the continuous-time stochastic signals include at least one multidimensional continuous-time signal, and wherein extracting one or more statistical features further comprises:
extracting a boundary of the lesion based on the at least one multidimensional continuous-time signal.

3. The method of claim 1, wherein the one or more statistical features include spatial information of the lesion, and wherein the spatial information of the lesion includes at least one of a symmetry of the lesion, a border of the lesion, one or more colors within the lesion, a number of different colors within the lesion, a diameter of the lesion, or a texture of the lesion.

4. The method of claim 1, further comprising:
generating a stochastic parametric description of the warm-up process.

5. The method of claim 1, further comprising:
estimating an autocorrelation function for the warm-up process;
estimating eigenfunctions and eigenvalues of the autocorrelation function of the warm-up process;
extracting Karhunen-Loève coefficients for the warming-up process based on the eigenfunctions; and
extracting projections of the warming-up profile onto temporal or spatio-temporal basis functions comprising the eigenfunctions.

6. The method of claim 5, further comprising:
modeling parameters of the autocorrelation function for the warm-up process using a multivariate random distribution model.

7. The method of claim 6, wherein determining a malignancy probability further comprises:
providing a predetermined number of eigenvalues and eigenfunctions from the autocorrelation function; and
forming a likelihood-ratio test.

8. The method of claim 7, wherein the predetermined number of eigenvalues and eigenfunctions is a whole number greater than one.

9. The method of claim 1, wherein the temporal profile includes a plurality of temperature gradients of the lesion.

10. The method of claim 1, wherein classifying the lesion further comprises:
classifying the lesion as at least one of a benign type or a malignant type.

11. A system for classifying lesions, comprising:
a cooling unit configured for applying to an area of skin comprising a lesion of a patient to initiate a warm-up process of the area of skin to an ambient temperature;
an infrared camera configured to receive a temporal sequence of thermal images of the area of skin representing a thermal recovery of the area of skin; and
an electronic computer communicatively coupled to the infrared camera and configured to generate a temporal profile of the thermal recovery based on the temporal sequence of thermal images, analyze temporal statistical properties of the temporal profile, determine a malignancy probability that the lesion is malignant based on an analysis of the temporal profile by extracting one or more statistical features based on continuous-time stochastic signals in the sequence of thermal images, and classify the lesion based on the malignancy probability.

12. The system of claim 11, wherein the continuous-time stochastic signals include at least one multidimensional continuous-time signal, and wherein the computer is further configured to extract the one or more statistical features by extracting a boundary of the lesion based on the at least one multidimensional continuous-time signal.

13. The system of claim 11, wherein the one or more statistical features include spatial information of the lesion, and wherein the spatial information of the lesion includes at least one of a symmetry of the lesion, a border of the lesion, one or more colors within the lesion, a number of different colors within the lesion, a diameter of the lesion, or a texture of the lesion.

14. The system of claim 11, wherein the electronic computer is further configured to generate a stochastic parametric description of the warm-up process.

15. The system of claim 11, wherein the electronic computer is further configured to:
estimate an autocorrelation function for the warm-up process;
estimate eigenfunctions and eigenvalues of the autocorrelation function of the warm-up process;
extract Karhunen-Loève coefficients for the warming-up process based on the eigenfunctions; and
extract projections of the warming-up profile onto temporal or spatio-temporal basis functions comprising the eigenfunctions.

16. The system of claim 15, wherein the electronic computer is further configured to model parameters of the autocorrelation function for the warm-up process using a multivariate random distribution model.

17. The system of claim 16, further configured to determine a malignancy probability by:
providing a predetermined number of eigenvalues and eigenfunctions from the autocorrelation function; and
forming a likelihood-ratio test.

18. The system of claim 17, wherein the predetermined number of eigenvalues and eigenfunctions is a whole number greater than one.

19. The system of claim 11, wherein the temporal profile includes a plurality of temperature gradients of the lesion.

20. The system of claim 11, wherein the electronic computer is further configured to classify the lesion by classifying the lesion as at least one of a benign type or a malignant type.

* * * * *